United States Patent [19]

Schwartz et al.

[11] Patent Number: 5,175,154
[45] Date of Patent: Dec. 29, 1992

[54] 5 α-PREGNAN-20-ONES AND 5-PREGNEN-20-ONES AND RELATED COMPOUNDS

[75] Inventors: Arthur G. Schwartz, Philadelphia; Marvin L. Lewbart, Media, both of Pa.

[73] Assignee: Research Corporation Technologies, Inc.

[21] Appl. No.: 126,310

[22] Filed: Nov. 25, 1987

[51] Int. Cl.$^5$ .................... A61K 31/58; A61K 31/56
[52] U.S. Cl. .................................. 514/172; 514/182; 514/909
[58] Field of Search ................... 260/397, 397.5; 552/541-544, 546, 551-552, 554-556, 559-560, 562, 564, 565, 567-568, 582-583, 585, 589, 599, 603-606, 609-616, 623-624, 650-652, 514, 536, 537-539, 548; G23/182, 172

[56] References Cited

U.S. PATENT DOCUMENTS

| | | | |
|---|---|---|---|
| 2,833,793 | 5/1958 | Dodson et al. | 514/178 |
| 2,911,418 | 11/1959 | Johns et al. | 514/178 |
| 3,131,125 | 4/1964 | Wettstein et al. | 514/182 |
| 3,148,198 | 9/1964 | Goldkamp et al. | 514/171 |
| 3,211,723 | 10/1965 | Kagan | 260/397.3 |
| 3,318,789 | 5/1967 | Jeger | 260/397.3 |
| 3,391,166 | 7/1968 | Klimstra | 514/171 |
| 3,471,480 | 10/1969 | Fritsch et al. | 514/178 |
| 3,471,526 | 10/1969 | Klimstra et al. | 514/171 |
| 3,639,598 | 2/1972 | Klimstra | 514/182 |
| 3,836,629 | 9/1974 | Klimstra | 514/182 |
| 3,890,356 | 6/1975 | Grunwell et al. | 260/397.5 |
| 3,914,265 | 10/1975 | Middleton | 552/557 |
| 3,976,691 | 8/1976 | Middleton et al. | 514/171 |
| 4,029,777 | 6/1977 | Engelfried et al. | 514/182 |
| 4,628,052 | 12/1986 | Peat et al. | 514/171 |

FOREIGN PATENT DOCUMENTS

| | | |
|---|---|---|
| 133995 | 3/1985 | European Pat. Off. . |
| 210665 | 2/1987 | European Pat. Off. . |
| 1239306 | 4/1964 | Fed. Rep. of Germany . |
| 2035738 | 6/1970 | Fed. Rep. of Germany . |
| 2705917 | 2/1977 | Fed. Rep. of Germany . |
| 2317934 | 2/1977 | France . |
| 989503 | 8/1963 | United Kingdom . |

OTHER PUBLICATIONS

*Remington's Pharmaceutical Sciences* (16th edition) 1980; pp. 420-435.
Bishop et al., J. Chem. Soc., Chem. Commun. (1983), pp. 123-124.
Pouzar et al., Collection Czech. Chem. Commun. (1981) 46, pp. 917-925.
Pouzar et al., Collection Czech. Chem. Commun. (1980) 45, pp. 2443-2451.
Gravestock et al., J. Amer. Chem. Soc., 102:2 (1980) pp. 800-807.
Bull et al., S.-Afr. Tydskr. Chem., (1979) 32(1) pp. 17-22.
Danilewicz et al., J. Chem. Soc. 1965 (Feb.) 1306-1319.
Malloux, et al., in Bulletin de la Societe Chemique de France, 617 (1969).
Pouzar et al. Chem. Abstracts 94:103670p (1980) "Steroids. Part CCXXXIV, Absolute Configuration at $C_{20}$ of the Derivatives of 21-Nor-52-Cholone-20,-24-Diol".
Danilewicz et al., CA 62: 91936 1965.
Gravestock et al. CA 92: 215624s 1980.
Hanson, et al., *Perkin Transactions I*, (1977), pp. 499-501.
Chemical Abstracts, 89, 1058656, (1978).
Numazawa, et al., *Steroids*, 32, 519-527 (1978).

(List continued on next page.)

*Primary Examiner*—Frederick E. Waddell
*Assistant Examiner*—Raymond J. Henley, III
*Attorney, Agent, or Firm*—Scully, Scott, Murphy & Presser

[57] ABSTRACT

Compounds of the formulae:

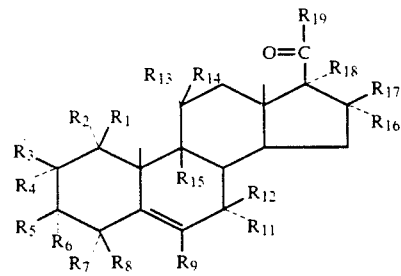

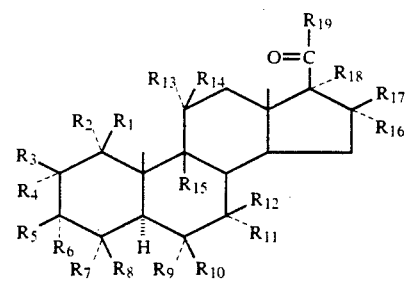

useful as anti-obesity, anti-diabetic, anti-coronary and hypolipidemic agents.

98 Claims, No Drawings

OTHER PUBLICATIONS

Swern, *Fels Report*, pp. 32-33 (date unknown).
Abou-Gharbia, et al., *Journal of Pharmaceutical Sciences*, 70, 1154 (1981).
Pashko, et al., *Carcinogenesis*, 2, 717-721 (1981).
Pashko, et al., *Carcingenesis*, 5, 463-466 (1984).
Raineri and Levy, *Biochemistry*, 9, 2233 (1970).
Robinson, et al., *J. Org. Chem.*, 28, 975 (1963).
Neef, et al., *J. of Org. Chem.*, 43, 4679-4680 (1978).
Gordon, et al., *Cancer Research* 46, 3389-3395 (1986).
Julian, et al., in *JACS*, 70, 3872-3876 (1948).
Ross, et al., in *J. Chem. Soc.*, 25 (1945).
Crabb, et al., in *J.C.S. Perkin I*, 1041 (1981).
Chemical Abstracts 92, 215616v (1980).
Bird, et al., in *J.C.S. Perkin I*, 750 (1980).
Kirk, et al., in *J.C.S. Perkin I*, 762 (1976).
Chemical Abstracts 79, 42723 (1973).
Denny, et al., in *J.C.S. Perkin I*, 486 (1972).
Bridgeman, et al., in *J. Chem. Soc.* C, 250 (1970).
Chemical Abstracts 67, 54331k (1967).
Catsoulacos, et al., in *J. Org. Chem.*, 32, 3723-3724 (1967).
Sheppard, et al., in *Some Chemistry of 13-Iso-Steroids*, 2551 (1977).
Pelc, et al., in *Collection Czechoslov. Chem. Commun.* 31, 1064 (1966).
Klimstra, et al., in *Journal of Med. Chem.*, 9, 924 (1966).
Bishop et al., CA 99:88445e 1983.
Pouzar et al., CA 95:187516z 1981.
Pradhan et al., CA 95:62499q 1981.
Bull et al., CA 92:111221s 1980.
Kocovsky et al., CA 90:204358r 1979.
Allinger, CA 65:5504d 1966.
Scherico, CA 69:97013s 1968.
Vandenheuvel, CA 85:59846t 1975.

5 α-PREGNAN-20-ONES AND 5-PREGNEN-20-ONES AND RELATED COMPOUNDS

BACKGROUND OF THE INVENTION

This invention relates to novel steroids and more particularly to 17-formyl and 17-alkanoyl derivatives of 5α-androstanes and 5-androstenes useful as anti-obesity, anti-diabetic, anti-coronary and hypolipidemic agents.

Dehydroepiandrosterone (DHEA) and DHEA-sulfate are major adrenal secretory products in humans. The plasma concentration of DHEA-sulfate, which next to cholesterol, is the most abundant steroid in humans, undergoes the most marked age-related decline of any known steroid.

Although DHEA-sulfate is the main precursor of placental estrogen and may be converted into active androgens in peripheral tissue, there is no obvious biological role for either DHEA or DHEA-sulfate in the normal individual. Several retrospective and prospective studies suggest that women with sub-normal levels of these steroids may be predisposed to develop breast cancer. For example, see Brownsey, et al., "Plasma dehydroepiandrosterone sulfate levels in patients with benign and malignant breast disease," Eur. J. Cancer, 8, 131-137 (1972); Bulbrook, et al., "Relation between urinary androgen and corticoid excretion and subsequent breast cancer," Lancet, 2, 395-398 (1971); Rose, et al., "Plasma dehydroepiandrosterone sulfate, androstenedione and cortisol, and urinary free cortisol excretion in breast cancer, "Eur. J. Cancer, 13, 43-47 (1977); Wang, et al., "Studies of the sulfate esters of dehydro-epiandorsterone and androsterone in the blood of women with breast cancer," Eur. J. Cancer, 10, 477–482 (1974); and Zumoff, et al., "Abnormal 24-hr mean plasma concentrations of dehydroisoandrosterone and dehydroisoandrosterone sulfate in women with primary operable breast cancer," Cancer Research, 41, 3360-3363, September, 1981.

It has also been established that DHEA is a potent non-competitive inhibitor of mammalian glucose-6-phosphate dehydrogenase (G6PDH). For example, see Oertel, et al., "The effects of steroids on glucose-6-phosphate dehydrogenase," J. Steroid Biochem., 3, 493-496 (1972) and Marks, et al., "Inhibition of mammalian glucose-6-phosphate dehydrogenase by steroids," Proc. Nat'l Acad. Sci, USA, 46, 477–452 (1960). Moreover, Yen, et al., "Prevention of obesity in A$^{vy}$/a mice by dehydroepiandrosterone," Lipids, 12, 409-413 (1977), reported that long-term administration of DHEA to VY-A$^{vy}$/a mice prevented the development of obesity without suppressing appetite.

Furthermore, it is also known that the long-term treatment of C3H mice with DHEA, in addition to reducing weight gain without suppressing appetite, markedly inhibits spontaneous breast cancer development and may delay the rate of aging. It has been observed that DHEA antagonizes the capacity of the tumor promoter, 12-O-tetradecanoylphorbol-13-acetate, to stimulate $^3$H-thymidine incorporation in mouse epidermis and in a cultured rat kidney epithelial cell line. See, Schwartz, "Inhibition of spontaneous breast cancer formation in female C3H-A$^{vy}$/a mice by long-term treatment with dehydroepiandrosterone, Cancer Res., 39, 1129-1132 (1979); and Schwartz, et al., "Dehydroepiandrosterone: an anti-obesity and anti-carcinogenic agent," Nut. Cancer 3, 46-53 (1981).

Ben-David, et al., "Anti-hypercholesterolemic effect of dehydroepiandrosterone in rats," Proc. Soc. Expt. Biol. Med., 125, 1136-1140 (1967) have observed that DHEA treatment has an anti-hypercholesterolemic effect in mice, while Coleman, et al. (Diabetes 31, 830, 1982) report that administration of DHEA produces a marked hypoglycemic effect in C57BL/KsJ-db/db mice. The latter authors suggest that the therapeutic effect of DHEA might result from its metabolism to estrogens.

It is further known that DHEA and 16α-bromoepiandrosterone are inhibitors of Epstein-Barr virus-induced transformation of human lymphocytes and that 16α-bromoepiandrosterone is a more potent inhibitor of mammalian G6PDH than DHEA. See, Schwartz, et al. Carcinogensis, Vol. 2 No. 7, 683–686 (1981).

While DHEA has been found effective in the afore-described manners, there is however, evidence of an estrogenic effect after prolonged administration. DHEA is not an estrogen per se but is well known to be convertible into estrogens. In addition, the therapeutic dose of DHEA is rather high. It would therefore be highly desirable to provide steroids, which while having the same afore-described advantage of DHEA are more potent and do not produce an estrogenic effect.

Besides DHEA, other steroids are known in the art. Great Britain Patent No. 989,503 to Burn, et al. discloses 6,16β-dimethyl-3β-hydroxyandrost-5-en-17-ones. These compounds are disclosed to be useful as possessing pituitary inhibiting action.

U.S. Pat. No. 2,833,793 to Dodson, et al. discloses 1β,3β-dihydroxy-5-androsten-17-one as an androgenic and anabolic agent.

U.S. Pat. No. 2,911,418 to Johns, et al. discloses 16α-chloro-3β-hydroxyandrost-5en-17-one and 3β-hydroxy-16α-iodandrost-5-en-17-one as an anti-androgen.

Goldkamp, et al. in U.S. Pat. No. 3,148,198 disclose that 16α,16β-difluoro-3β-hydroxyandrost-5-en-17-one possess androgenic properties.

French Application No. FR-A 2,317,934 discloses the following compounds:
3β-hydroxy-16ξ-methylandrost-5-en-17-one
3β-hydroxy-16ξ-ethylandrost-5-en-17-one
3β-hydroxy-16ξ-isopropylandrost-5-en-17-one U.S. Pat. No. 3,976,691 discloses the following compounds:

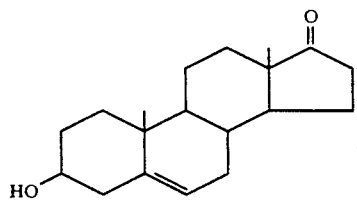

(a)

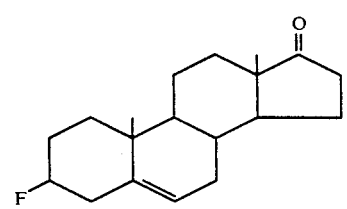

(b)

U.S. Pat. No. 3,471,480 to Fritsch, et al. discloses the following compounds which are useful as progestational agents:
(a) 3β-iodo-Δ⁵-6-methyl-17-oxoandrostene
(b) 3β-chloro-Δ⁵-6-methyl-17-oxoandrostene
(c) 3β-hydroxy-Δ⁵-6-methyl-17-oxoandrostene Hanson, et al. in Perkin Transactions I, 1977, pp. 499–501, disclose 3β,4β-dihydroxyandrost-5-en-17-one. No utility is disclosed.

Chemical Abstract 89:105866b discloses that 3β-hydroxy-5α-androstan-17-one can be hydroxylated in the 15α-position. Furthermore, said reference teaches that hydroxylation of 3β-hydroxy-5αandrosten-17-one gave both the 7α and 7β-hydroxyisoandrosterones.

Numazawa, et al. in *Steroids*, 32, 519–527 disclose 3β,16α-dihydroxyandrost-5-en-17-one. No utility is disclosed.

DE-A- 2,035,738 discloses 7α-Methyl-3β-hydroxy-5-androsten-17-one and 6,7α-dimethyl-3β-hydroxy-5-androsten-17-one.

DE-A2 705917 discloses 3β,16β-dihydroxy-5-androsten-17-one.

The Annual Report of the Fels Research Institute, pp. 32–33, (1979–1980) discloses the following compounds as having tumor-preventive, anti-obesity and anti-aging qualities:
3β-hydroxy-16α-bromo-5α-androstan-17-one
3β-hydroxy-16α-chloro-5α-androstan-17-one
3β-hydroxy-16α-fluoro-5α-androstan-17-one
3β-hydroxy-16α-iodo-5α-androstan-17-one
3β-hydroxy-16α-bromoandrost-5-ene-17-one
16αbromoandrostan-17-one Abou-Gharbia, et al. in *Journal of Pharmaceutical Sciences*, 70, 1154–1156 (1981) disclose the syntheses of:
3β-hydroxy-16α-chloro-5α-androstan-17-one.
3β-hydroxy-16α-fluoro-5α-androstan-17-one.
3β-hydroxy-16α-bromo-5α-androstan-17-one.
3β-hydroxy-16α-iodo-5α-androstan-17-one.

Pashko, et al. in *Carcinogenesis*, 2, 717–721 (1981) disclose that 16α-Br-epiandrosterone is more active than DHEA in inhibiting G6PDH and in reducing the rate of [³H] thymidine incorporation into mouse breast epithilum and epidermis. The authors suggest that this compound may be useful in suppressing breast cancer development.

Neef, et al. in *Journal of Org. Chem.*, 43, 4679–4680 disclose the syntheses of 3β-hydroxy-16α-methyl-5-androsten-17-one and 3β-hydroxy-16β-methyl-5-androsten-17-one.

Robinson, et al. in *Journal of Org. Chem.*, 28, 975–980 (1963) disclose the synthesis of 3β-hydroxy-16α, 16β-difluoro-5-androsten-17-one, and 16-formyl-5-androstene-3βol-17-one.

Ranier, et al. in *Biochemistry*, 9, 2233–2243 (1970) tested the inhibitory activity of the following steroids on NADP and NAD linked activity of glucose 6-phosphate dehydrogenase:
3β-Hydroxy-5-pregnen-20-one
3β, 17α-Dihydroxy-5α-pregnan-20-one
3β-Hydroxy-5α-pregnan-20-one
3β-Hydroxy-5β-pregnan-20-one
4-Pregnene-3,20 -dione
3β, 21-Dihydroxy-5-pregnen-20-one
3β-Hydroxy-16α,17α-epoxy-5-pregnen-20-one
3β-Hydroxy-6-methyl-5-pregnen-20-one
3β-Hydroxy-16α-bromo-5-pregnen-20-one Gordon, et al. in Cancer Research 46, 3389–3395 (1986) disclose that DHEA, 16α-bromoepiandrosterone, epiandrosterone, 3β-hydroxy-5α-pregnan-20-one, 5α-androstan-17-one and 5α-androstan-3β,16α-diol-17-one are inhibitors of glucose 6-phosphate dehydrogenase. Furthermore, said reference discloses that testosterone, 17β-Estradiol, 5-androstene-3β,17βdiol, dehydroepiandrosterone-3-sulfate and 5α-androstan-17β-ol are noninhibitors of glucose-6-phosphate dehydrogenase. The reference suggests that there is a general correlation between the structure requirements for blocking differentiation to adipocytes and inhibiting glucose-6-phosphate dehydrogenase.

Julian, et al. in *JACS*, 70, 3872–3876 (1948) discloses the preparation of 16-dimethylaminomethyldehydroisoandrosterone and 16-methylenedehydroisoandrosterone acetate.

Ross, et al. in J. Chem. Soc., 25, (1945) disclose the synthesis of 16-isopropylidene-5-androstene-17-one.

Peat in U.S. Pat. No. 4,628,052 disclose compositions containing the following compound as the active ingredient:

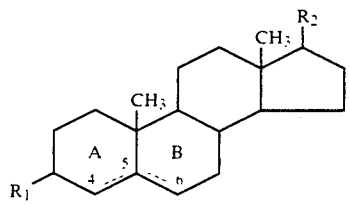

wherein R₁ is O or OH and R₂ is O, or OH; and which may contain one double bond in ring A and/or ring B or tocopherol.

The compounds are alleged to be useful in treating rheumatoid arthritis, osteoarthritis and arthritis associated with psoriasis and with lupus and other autoimmune diseases and also for treating non-specific joint pain associated with stress.

SUMMARY OF THE INVENTION

The present invention relates to novel steroids which are useful as anti-obesity agents, anti-hyperglycemic agents, anti-hypercholesterolemic agents and anti-autoimmune agents.

Moreover, the present invention is directed to novel steroids, useful as anti-obesity, anti-hyperglycemic, and anti-hypercholesterolemic agents, which do not evidence estrogenic effects.

Finally, the present invention is directed to the process for the treatment and/or prevention of obesity, diabetes and hyperlipidemia.

Therefore, the present invention provides novel steroids of the general formula:

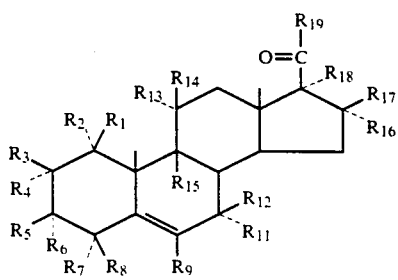

wherein $R_1$, $R_2$, $R_3$, $R_4$, $R_5$, $R_6$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;

$R_9$ is hydrogen, lower alkyl or halogen;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl, with the proviso that when $R_{19}$ is methyl and $R_1$, $R_2$, $R_3$, $R_4$, $R_7$, $R_8$, $R_9$, $R_{11}$, $R_{12}$, $R_{13}$, $R_{14}$, $R_{15}$, $R_{16}$, $R_{17}$ and $R_{18}$ are hydrogen or when $R_{19}$ is methyl, $R_{16}$ and $R_{18}$ taken together with the carbon to which they are attached form an epoxide ring and $R_1$, $R_2$, $R_3$, $R_4$, $R_7$, $R_8$, $R_9$, $R_{11}$, $R_{12}$, $R_{13}$, $R_{14}$, $R_{15}$ and $R_{17}$ are hydrogen, or when $R_{19}$ and $R_9$ are methyl and $R_1$, $R_2$, $R_3$, $R_4$, $R_7$, $R_8$, $R_{11}$, $R_{12}$, $R_{13}$, $R_{14}$, $R_{15}$, $R_{16}$, $R_{17}$ or $R_{18}$ are hydrogen or when $R_{16}$ is bromo, $R_{19}$ is methyl and $R_1$, $R_2$, $R_3$, $R_4$, $R_5$, $R_7$, $R_8$, $R_9$, $R_{11}$, $R_{12}$, $R_{13}$, $R_{14}$, $R_{15}$, $R_{17}$ and $R_{18}$ are hydrogen, then neither $R_5$ nor $R_6$ is hydroxy.

Further objectives are accomplished herein by providing novel steroids of the formula:

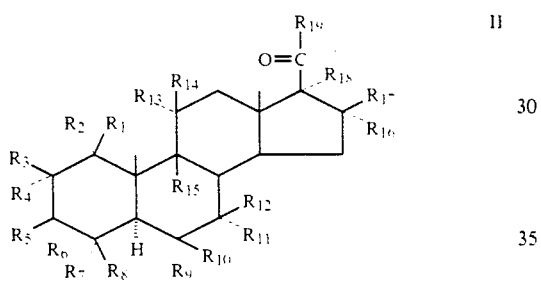

wherein $R_1$, $R_2$, $R_3$, $R_4$, $R_5$, $R_6$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;

$R_9$ and $R_{10}$ are each independently hydrogen, lower alkyl or halogen;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl, with the proviso that when $R_{19}$ is methyl and $R_1$, $R_2$, $R_3$, $R_4$, $R_7$, $R_8$, $R_9$, $R_{10}$, $R_{11}$, $R_{12}$, $R_{13}$, $R_{14}$, $R_{15}$, $R_{16}$, $R_{17}$ and $R_{18}$ are hydrogen or when $R_{19}$ is methyl, $R_{18}$ is hydroxy, and $R_1$, $R_2$, $R_3$, $R_4$, $R_7$, $R_8$, $R_9$, $R_{11}$, $R_{12}$, $R_{13}$, $R_{14}$, $R_{15}$, $R_{16}$ and $R_{17}$ are hydrogen, then neither $R_5$ nor $R_6$ is hydroxy.

The present invention is also directed to processes for the prophylaxis of obesity, diabetes and hyperlipidemia and autoimmune diseases, such as lupus erthematosus or Coomb's positive hemolytic anemia, by administering to a host, e.g., mammals, a therapeutically effective amount of the afore-identified steroids.

DETAILED DESCRIPTION OF THE INVENTION

In accordance with the present invention, it has been surprisingly discovered that steroids having a certain structure, described hereinafter in more detail, are characterized with significant pharmacological properties without toxic or undesirable estrogenic effects. That is, it has been quite unexpectedly discovered that the steroids of the present invention are useful as anti-obesity, anti-diabetic, and anti-hypercholesterolemic agents, but unlike DHEA are more potent and exhibit very little or no estrogenic effects.

More particularly, the steroids of the present invention have the general formulae:

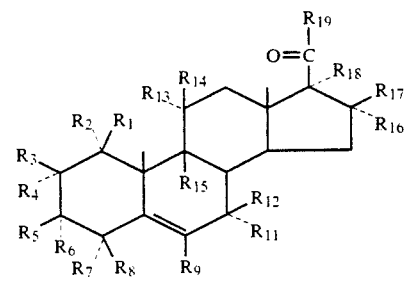

and

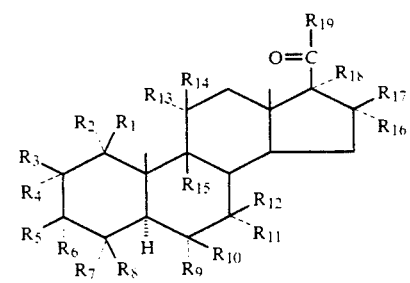

wherein $R_1$–$R_{19}$ are as defined hereinbefore. The $R_1$–$R_{18}$ substituents are designated as being in the α-position by means of a broken line (---) joining the substituent to the steroid nucleus, the substituents are designated as being in the β-position by means of a solid line (—) joining the substituent to the steroid nucleus and in those cases in which the substituent may be either in the α- or β-position the substituents are indicated as being joined to the steroid nucleus by a wavy line. Furthermore, in accordance with I.U.P.A.C. nomenclature, the carbon atoms of the steroids of the present invention are numbered as follows and the steroids have the designated I.U.P.A.C. stereochemistry:

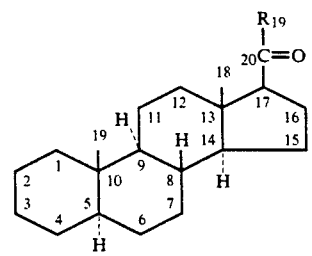

The present invention provides processes for the prophylaxis of obesity, diabetes, and hyperlipidemia and autoimmune diseases, such as lupus erythematosus or Coomb's positive hemolytic anemia comprising administering to a host, e.g., mammals, a therapeutically effective amount of the present new steroids.

In accordance with the present invention, it has been surprisingly discovered that steroids having a certain structure, described hereinabove and hereinafter in more detail, are characterized with significant pharmacological properties without toxic or undesirable estrogenic effects. That is, it has been quite unexpectedly discovered that the steroids of the present invention are useful as, anti-obesity, anti-diabetic, anti-autoimmune and anti-hypercholesterolemic agents, but unlike DHEA are more potent and exhibit very little or no estrogenic effect. Furthermore, unlike DHEA, compounds of the present invention do not induce liver enlargement and increased catalase activity.

Preferred embodiments of the compounds of Formula I have the formula:

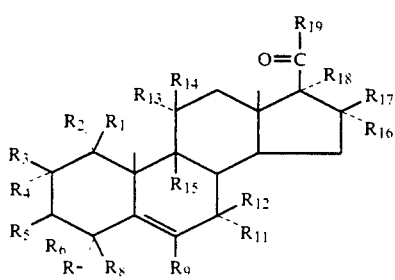

III wherein $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;

$R_5$ and $R_6$ are independently hydrogen, lower alkyl, halogen or lower alkoxy;

$R_9$ is hydrogen, lower alkyl or halogen;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

Especially preferred compounds of Formula I have the formula:

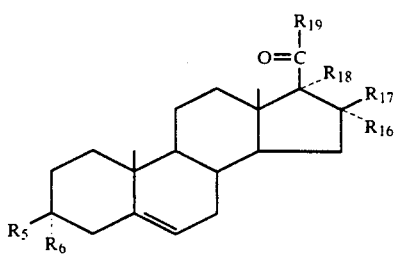

IV wherein $R_5$ and $R_6$ are independently hydrogen or lower alkyl;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

The most preferred embodiment of Formula I has the formula:

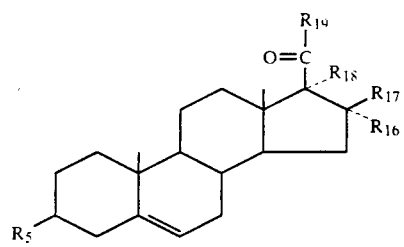

V wherein $R_5$ is hydrogen or lower alkyl;

$R_{16}$ and $R_{17}$ are independently hydrogen, lower alkyl, halogen, hydroxy or lower alkoxy; or $R_{18}$ is hydrogen, lower alkyl, halogen or lower alkoxy;

$R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

Preferred compounds of Formula II have the formula:

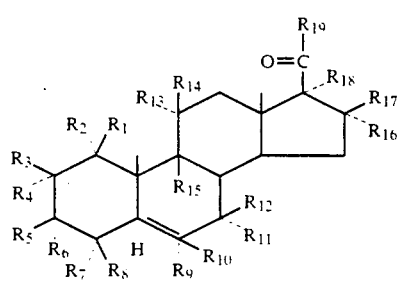

VI wherein $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen hydroxy or lower alkoxy;

$R_5$ and $R_6$ are independently hydrogen, lower alkyl, halogen or lower alkoxy;

$R_9$ and $R_{10}$ are each independently hydrogen, lower alkyl or halogen;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

Especially preferred embodiments of Formula II have the formula:

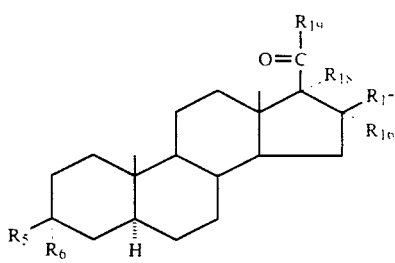

VII wherein $R_5$ and $R_6$ are independently hydrogen or lower alkyl;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

The most preferred embodiment of Formula II has the formula:

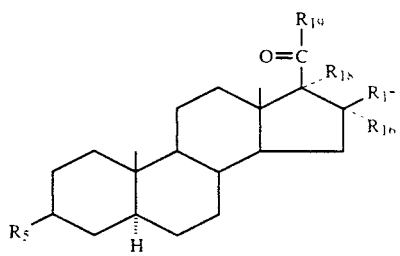

VIII wherein $R_5$ is hydrogen or lower alkyl;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

In the present invention, the alkyl groups are preferably lower alkyl, which may be straight or branched chain, and which contain up to 6 carbon atoms. Examples include methyl, ethyl, propyl, isopropyl, butyl, isobutyl, pentyl, amyl and the like. A preferred alkyl group contains 1-3 carbons. The most preferred alkyl group is methyl.

The halo atoms are preferably Br, F or Cl, especially F.

Moreover, it is preferred that at most one of the substituents, $R_1$, $R_2$, $R_3$, $R_4$, $R_7$, $R_8$, $R_9$, $R_{10}$, $R_{11}$, $R_{12}$, $R_{13}$, $R_{14}$ or $R_{15}$ is other than hydrogen. In the most preferred embodiment, $R_1$, $R_2$, $R_3$, $R_4$, $R_7$, $R_8$, $R_9$, $R_{10}$, $R_{11}$, $R_{12}$, $R_{13}$, $R_{14}$ and $R_{15}$ are hydrogen.

In all of the compounds described hereinabove, it is preferred that $R_5$ and $R_6$ are independently hydrogen or lower alkyl. In the most preferred embodiment $R_5$ is hydrogen or lower alkyl and $R_6$ is hydrogen. The most preferred alkyl group of $R_5$ is methyl.

In addition, it is preferred that $R_{18}$ is hydrogen or fluorine; $R_{16}$ is hydrogen, fluorine or methyl; $R_{17}$ is hydrogen or methyl or $R_{16}$ and $R_{18}$ taken together to the carbon to which they are attached form an epoxide ring. The most preferred $R_{19}$ is hydrogen, trifluoromethyl, difluoromethyl, monofluoromethyl or methyl.

Additional variations in the structural formula representing the instant compounds can be effected without significantly altering the therapeutic properties. For example, the alkyl moieties can be substituted by one or more of a variety of substituents, such as hydroxy, halogen, alkyl and the like.

The procedures described hereinbelow are representative of the processes for preparing compounds of the present invention. For example, even though the procedures are shown for the preparation of compounds wherein $R_{19}$ is $CH_3$, the procedures are also applicable for the preparation of other compounds within the scope of the present invention. Furthermore, the procedures described hereinbelow are also applicable to those steroids which have additional substituents than those depicted hereinbelow. If substituents on the steroidal ring are themselves reactive under the reaction conditions then these substituents can themselves be protected according to chemical techniques known in the art. A variety of protecting groups known in the art may be employed. Examples of many of these possible groups may be found in "Protective Groups in Organic Synthesis," by J. W. Green, John Wiley and Sons, 1981.

If more than one substituent is to be added to the steroidal ring, the substituents can be added in any order, except it is preferred that halogens are added last.

Finally, the procedures described hereinbelow are applicable to all the steroids of the present invention, regardless of whether a double bond is present in the 5,6 position of the steroidal ring. Moreover, those steroids of Formula II can be prepared from the corresponding steroids of Formula I by techniques known to one skilled in the art, e.g., by catalytic hydrogenation using, e.g., $H_2/Pd$, $H_2/Pt$ or $H_2/Ni$.

The steroids of the present invention may be prepared in accordance with conventional organic synthesis from known compounds or readily preparable intermediates.

The Pregnanes and Pregnenes can be prepared by techniques known in the art. An exemplary procedure is as follows:

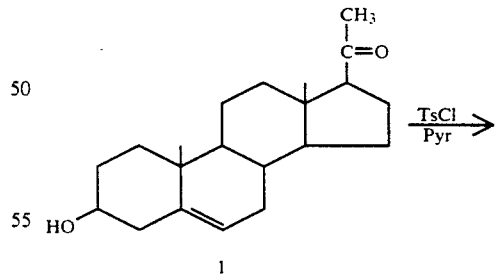

1

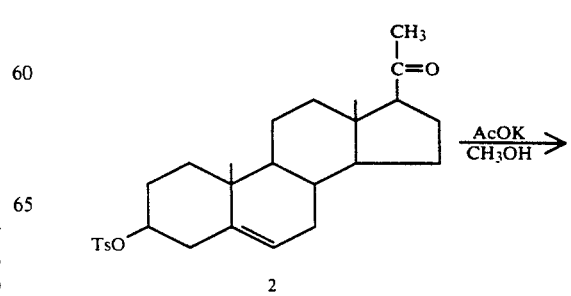

2

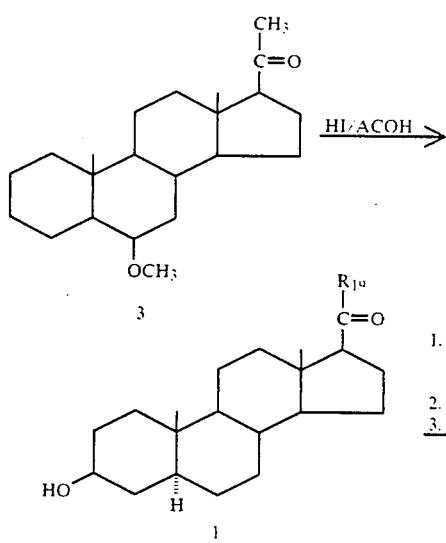
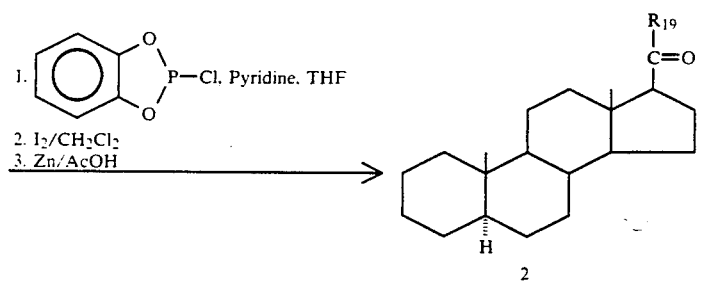
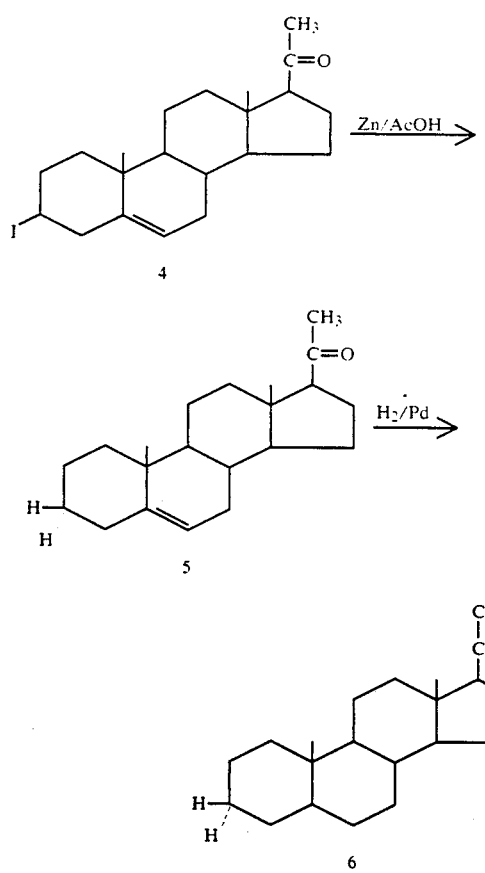

2 is placed in methanol and reacted with potassium acetate to form the methoxy substituent (3). Hydrogen iodide addition to 3 produces the 3B-iodide derivative (4). Reaction of 4 with Zn/AcOH produces the desoxy derivative 5. Catalytic hydrogenation of 5 produces 6.

Preparation of 3-Desoxy Compounds

The 3-desoxy compounds are prepared from the corresponding 3-hydroxy compounds by techniques known in the art. For example, In other words, the 3β-OH compound, such as 3β-hydroxy-5α-pregnan-20-one, is dissolved in an inert solvent, such as methylene chloride and reacted with O-phenylene phosphorohloroidite. The resulting product was reacted with iodine to form the 3-iodo derivative which in turn is reached with a Lewis acid, such as zinc in acetic acid, to form the corresponding 3-desoxy compound.

ALKYLATION

CARBON-1-ALKYLATION

A representative procedure for alkylation at carbon-1 is given in Scheme 1.

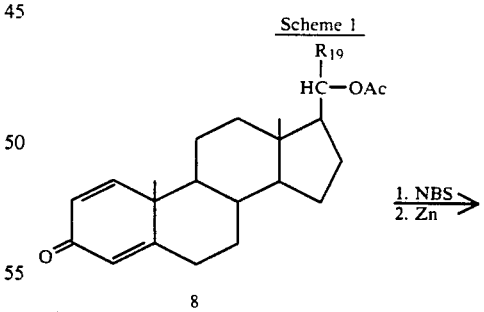
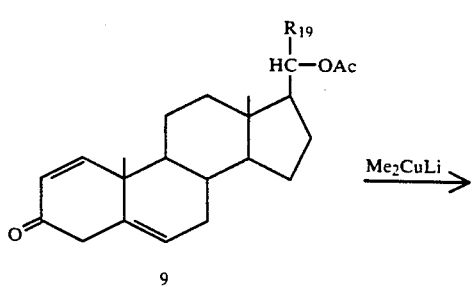

The $\Delta^5$-3B-ol is placed in a suitable solvent, such as pyridine with p-toluene sulfonyl chloride and reacted at room temperature. Approximately 2 liter of ice and water is added to quench the reaction. The product is filtered off and washed, and the tosylate product (2) is isolated.

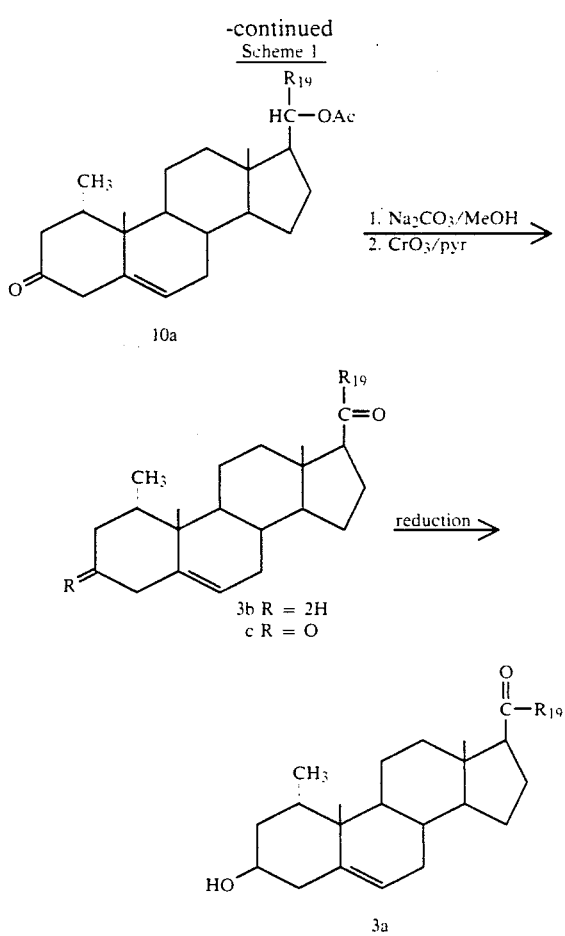

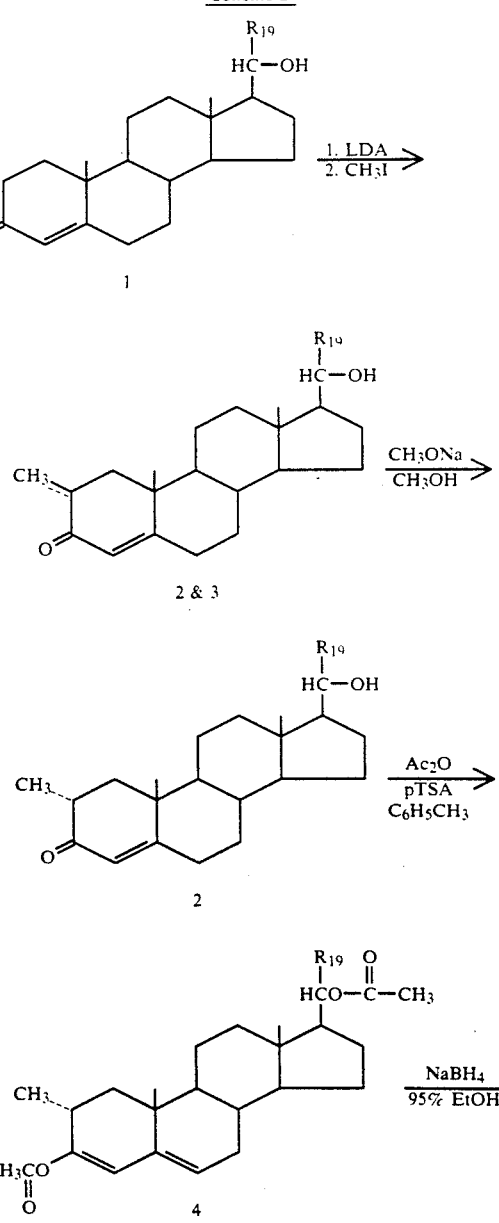

tion of 2 with an acetylating agent. such as acetic anhydride (Ac₂O) and p-toluenesulfonic acid (p-TSA) in toluene affords the 2α-methyl 3,20 dihydroxy-3,5-pregnadien-3,20-diacetate (4). Treatment of the diacetate (4) with sodium borohydride in 95% ethanol yields 2α-methyl-3β,20β-dihydroxy-5-pregnene-20-acetate (5). Protection of the 3-hydroxy group as a tetrahydropyranyl ether followed by hydrolysis of the 20-acetate yields 2α-methyl-3β,20β-dihydroxy-5-pregnene-3-tetrahydropyranyl ether 7. Oxidation of the C-20 hydroxy group in 7 followed by hydrolysis of the tetrahydropyranyl ether with hydrochloric acid and aqueous acetone yielded 3β-hydroxy-2α-methyl-5-pregnen-17-one. (9).

Allylic bromination (e.g. with N-bromosuccinimide (NBS)) of 20β-acetoxypregn-1,4-dien-3-one, for example, followed by treatment with zinc affords the nonconjugated enone 9. 1,4-Alkylation with lithiodimethyl cuprate provides the 1α-methyl ketone 10a. At this stage the 10a may be converted to a methylene by Wolff-Kishner reduction or the Huang Minlon modification thereof. These vigorous reaction conditions result in hydrolysis of the resulting carbon-20-acetate thereby yielding the hydroxy derivative, 3β-hydroxyα-methyl-5-pregnene-20-one (3b). Both 10a and its desoxy derivative can be converted via standard reactions, i.e., hydrolysis of the 20-acetate with sodium carbonate and methanol followed by chromium trioxide oxidation of the resulting 20-alcohol to the carbon-20 ketone. Selective reduction of the carbon-3 ketone, 3,20-diketone 3c using sodium borohydride pyridine (pyr) yields the 1α-methyl derivative 3a.

CARBON-2-ALKYLATIONS

The following procedures are illustrative for alkylation at carbon-2 and are figuratively illustrated in Scheme 2 below.

Alkylation of (1), such as 20-hydroxy-4-pregnen-3-one, with an alkylating agent, such as methyl iodide, in the presence of a strong base, such as t-BuOK, sodium t-pentoxide, lithium diisopropylamide (LDA), Na NH₂, Et₂Ni, n-butyl lithium and the like gives a mixture of the 2α- and 2β-alkyl-20-β-hydroxy derivatives (2 and 3). Treatment of the mixture with a strong base, such as sodium methoxide in methanol, epimerizes the 2β-axial alkyl to the 2-α-equitorial configuration (2). Acetyla- -continued
Scheme 2

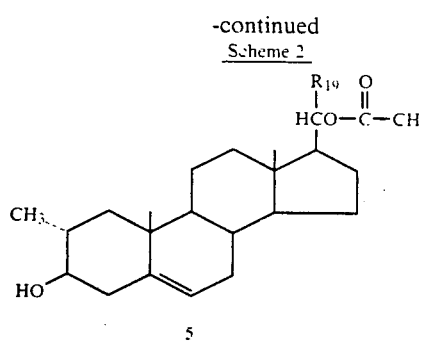

5

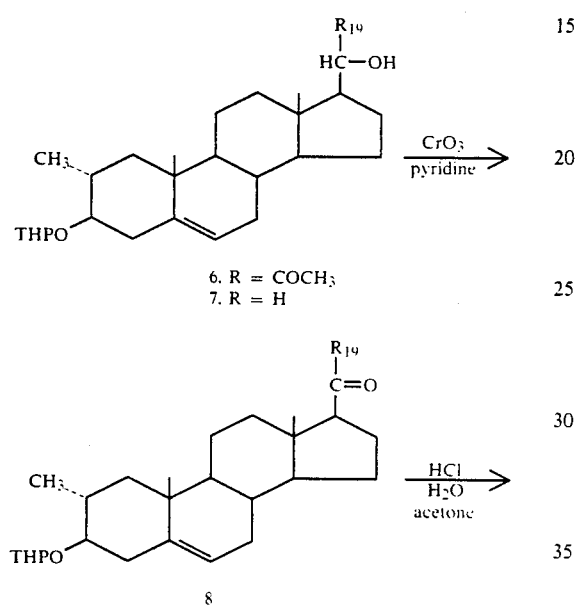

6. R = COCH₃
7. R = H

8

9

CARBON 3-ALKYLATIONS

The schematic for carbon 3-alkylations are shown figuratively in scheme 3 below.

Synthesis of 3-alkyl-5-pregnene-20-one, e.g., with a methyl group replacing the hydroxyl group at carbon-3 is shown below in scheme 3. The methyl configuration at carbon-3 is $\beta$, as determined by X-ray analysis. 3$\beta$-Hydroxy-5-pregnen-17-one (10) is iodinated at carbon-3 with O-phenylenephosphorochloridite followed by decomposition of the resulting phosphite ester with iodine. 3$\beta$-Iodo-5-pregnen-17-one (11) is ketalized, then alkylated with a mixture of methyl lithium and cuprous cyanide in tetrahydrofuran to yield 3$\beta$-methyl-5-pregnen-20-ethylene ketal (13). Hydrolysis of the ketal affords 3$\beta$-methyl-5-pregnen-17-one (14).

Scheme 3

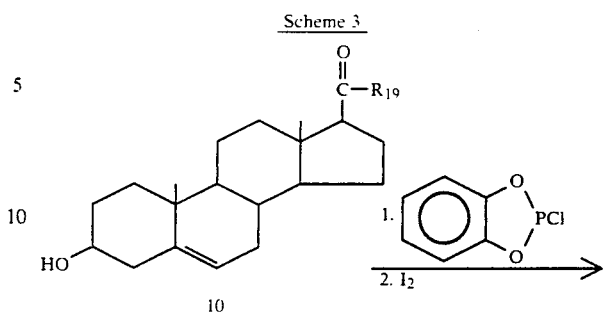

10

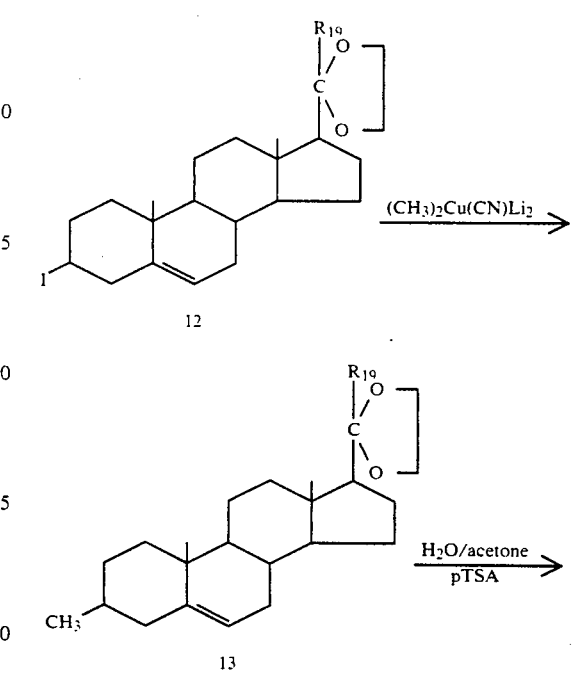

11

12

13

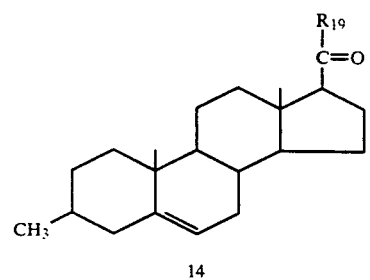

14

ALKYLATION AT CARBON-4

A procedure for carbon-4 alkylation is given in Scheme 4.

Scheme 4

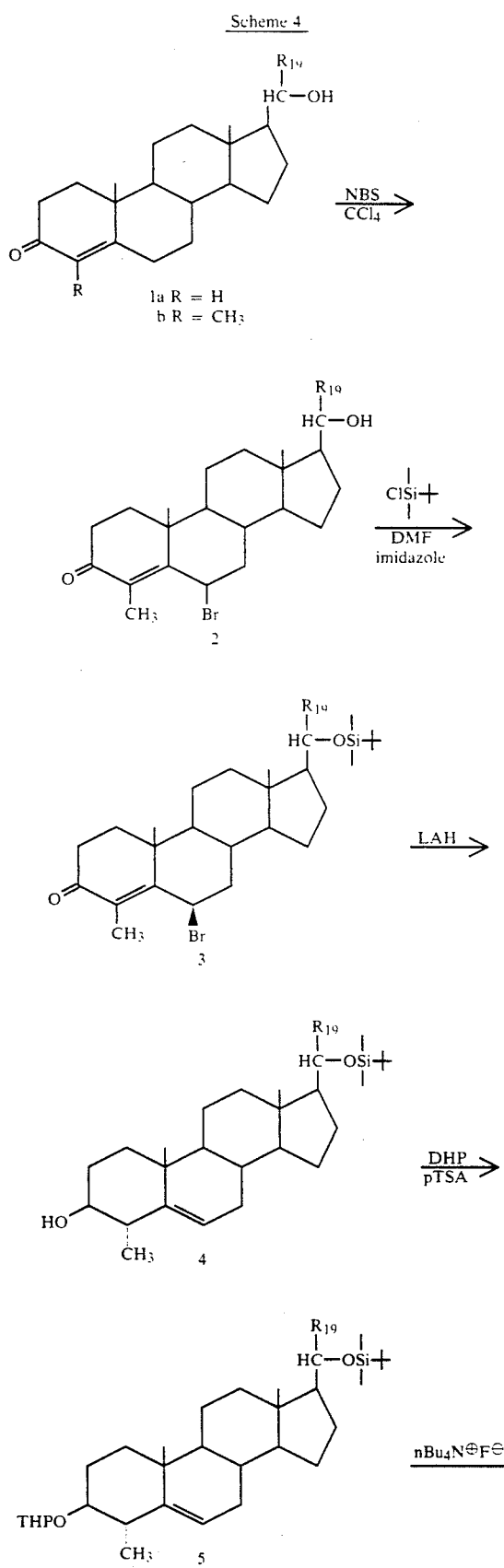

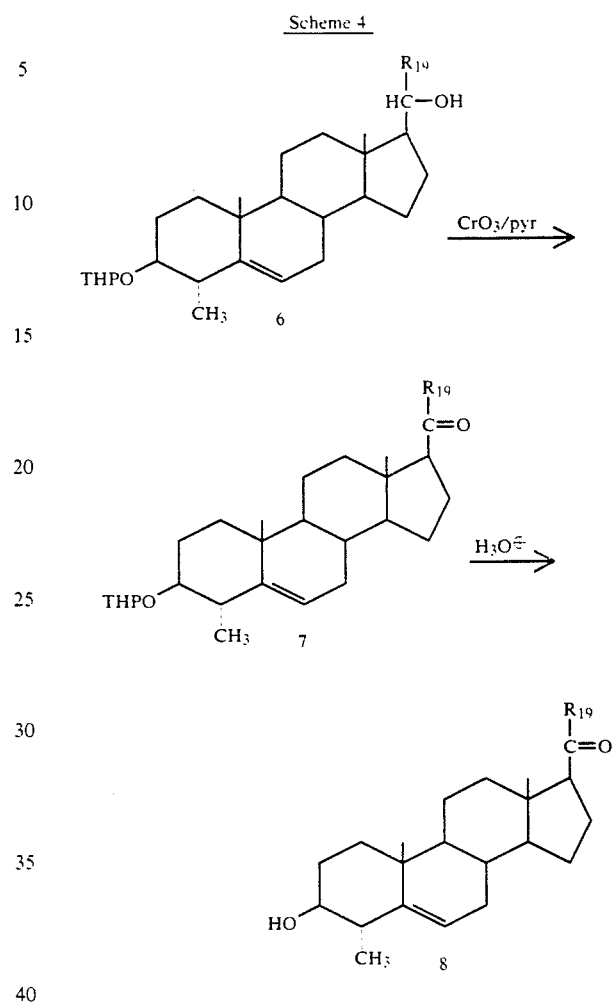

With reference to Scheme 4, alkylation of 1a, such as 20-hydroxy-4-pregnen-3-one, using potassium t-butoxide and methyl iodide yields 4-methyl-20-hydroxy-4-pregnen-3-one 1b. Allylic bromination of N-bromosuccinimide in carbon tetrachloride yields the 6β-bromo derivative. Protection of the C-20 alcohol as its t-butyl-dimethyl silyl derivative yields 3. Lithium aluminum hydride reduction of the ketone in 3 with concomitant double bond migration and loss of bromide should yield 4. Protection of the C-3 alcohol as a tetrahydropyranyl ether, followed by deprotection and oxidation of the C-17 alcohol should yield the C-17 ketone 7. Removal of the C-3 tetrahydropyranyl ether yields 4α-methyl-5-pregnen-20-one.

ALKYLATION AT CARBON-6

Steroids may be alkylated at carbon-6 using the method of U. Stache and W. Fritsch, *Liebigs Analen* 1966, 697, 204.

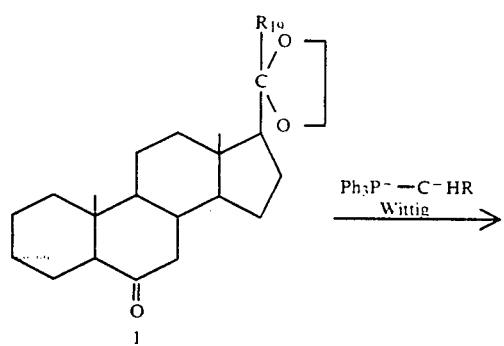

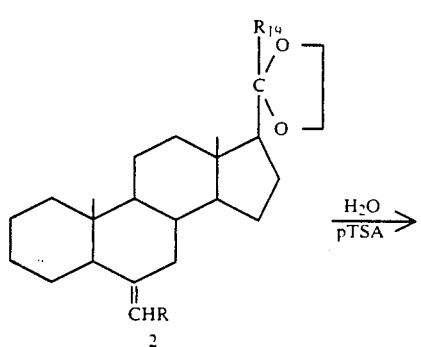

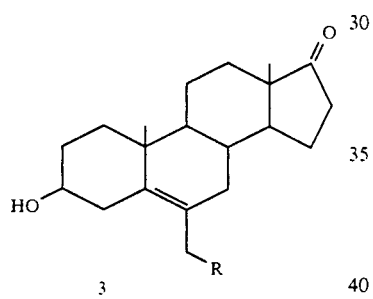

3α,5-cyclosteroids, such as 3α,5-cyclo-5α-pregnan-6,20-dione-20-ketal 1 are readily available by solvolysis of steroidal 5-ene-3β-tosylates and mesylates followed by oxidation of the C-6 hydroxyl group. Methylenation of 1 affords 6-methylene-3α,5-cyclo-5α-pregnan-20-one-20-ketal 17-ketal 2 (R=H). Treatment of 2 with aqueous acid results in the addition of water and the formation of 3β-hydroxy-6-methyl-5-pregnen-20-one, 3 (R=H).

ALKYLATION AT C-7

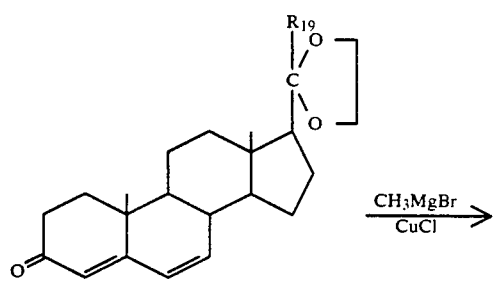

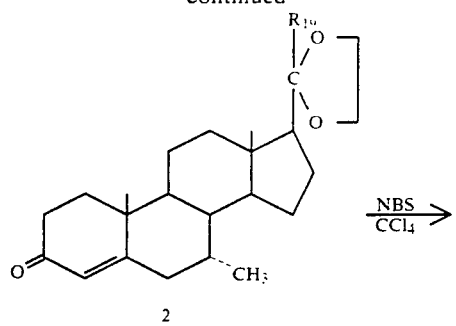

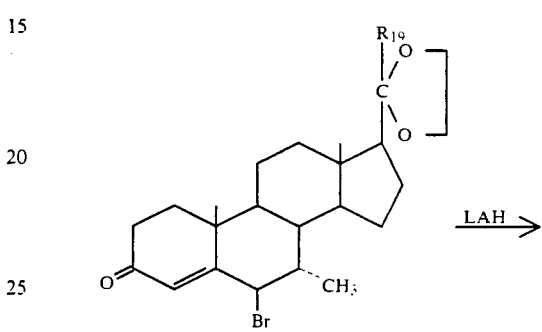

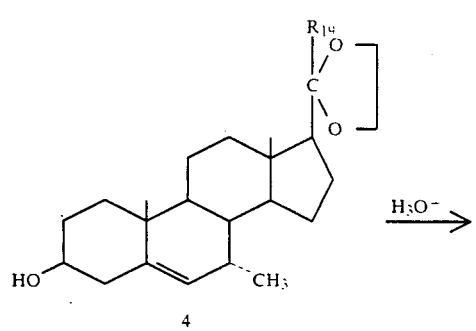

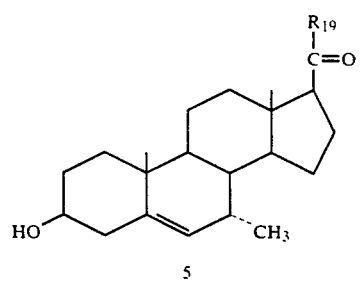

Alkylation of, e.g., pregna-4,6-dien-3,20-dione-20-ketal with methyl magnesium bromide in the presence of cuprous chloride, proceeds via conjugate addition to yield 7α-methyl-5-pregnen-3,20-dione-20-ketal 2. Allylic bromination of 2 using N-bromosuccinimide in carbon tetrachloride yields the 6β-bromo-7α-methyl-5-pregnen-3,20-dione 20 ketal 3. Lithium aluminum hydride reduction of the ketone in 3 with concomitant double bond migration and loss of bromide should yield 4. Deprotection of the C-20 ketone with aqueous acid yields 3β-hydroxy-7α-methyl-5-pregnen-20-one, 5. Higher homologues may be synthesized using the substituted Grignard reagent, i.e., R=$CH_3$, $C_2H_5$, $C_3H_7$. The 7β-epimer can be synthesized by treatment of 2 with DDQ--dichlorodicyanoquinone to generate another olefin at C-7. Catalytic reduction of this olefin should occur from the α face of the steroid to yield the 7β-methyl steroid, i.e., 7β-methyl-5-pregnen-3,20-dione-20-ketal. Following the same sequence as above yields 3β-hydroxy-7β-methyl-5-pregnen-20-one.

ALKYLATION AT CARBON-11

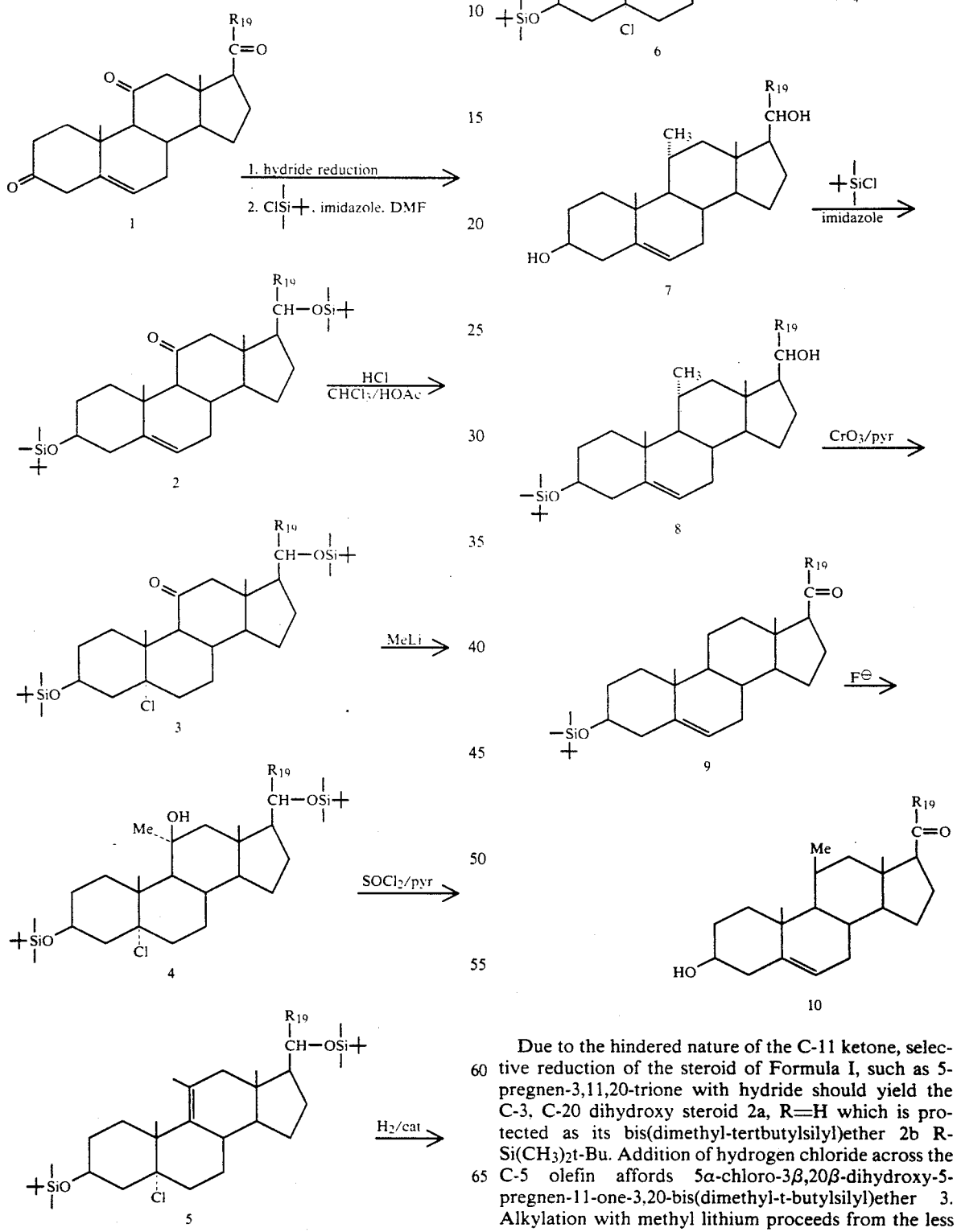

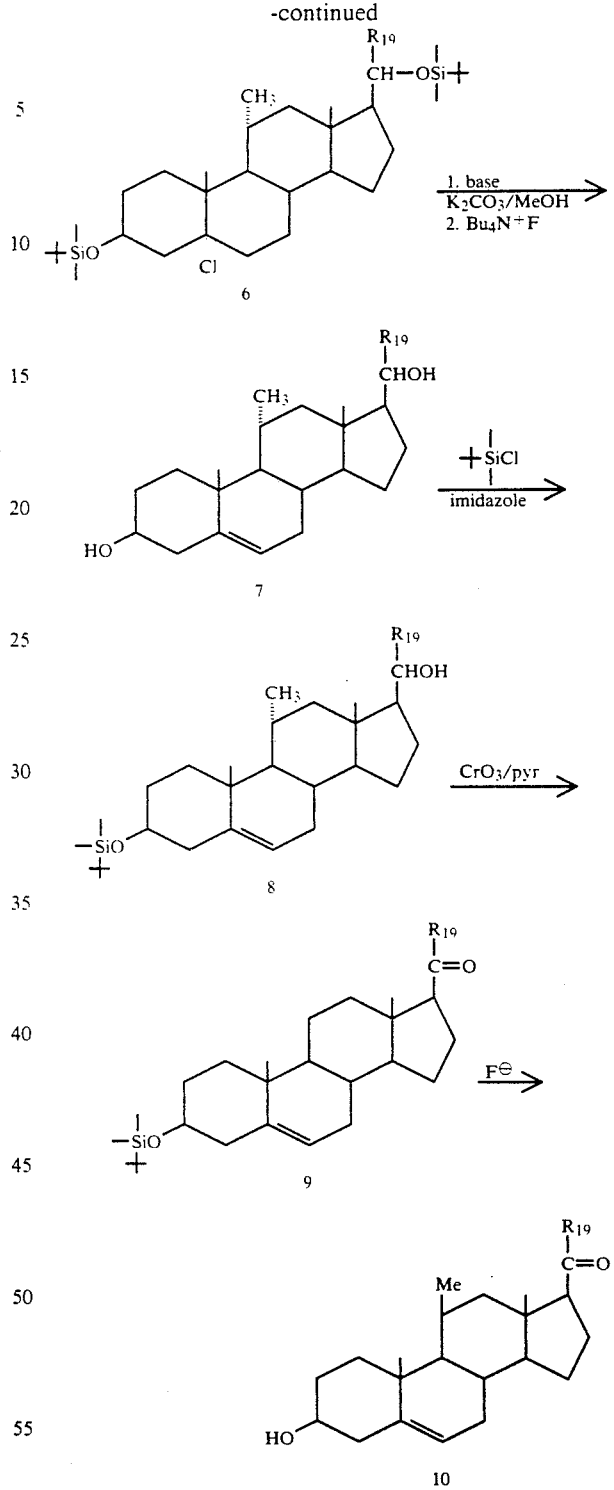

Due to the hindered nature of the C-11 ketone, selective reduction of the steroid of Formula I, such as 5-pregnen-3,11,20-trione with hydride should yield the C-3, C-20 dihydroxy steroid 2a, R=H which is protected as its bis(dimethyl-tertbutylsilyl)ether 2b R-Si(CH$_3$)$_2$t-Bu. Addition of hydrogen chloride across the C-5 olefin affords 5α-chloro-3β,20β-dihydroxy-5-pregnen-11-one-3,20-bis(dimethyl-t-butylsilyl)ether 3. Alkylation with methyl lithium proceeds from the less hindered α face to yield 5α-chloro-11α-methyl pregnen-3β,11β,20β-triol-3,20-bis(dimethyl-t-butylsilyl)ether 4. Dehydration of the methylcarbinol 4 with thionyl chloride in pyridine provides the olefin 5. Catalytic hydrogenation of 5 gives the saturated 11α-methyl-5αchloro-bis (silyl) ether 6. Treatment of the chloro silyl ether 6 with base followed by tetrabutyl ammonium fluoride affords 11α-methyl-5-pregnen-3β,20β-diol 7. Selective silylation yields 11α-methyl-5-pregnen-3β,20β-diol 3-dimethyl t-butylsilyl ether 8. Oxidation of the C-20 alcohol in 8 yields 9 and deprotection of the 3-alcohol yields 11α-methyl-5-pregnen-3β-ol-20-one 10.

The following procedures illustrate hydroxylation at Carbon-1, 2, 4, 7, 11 or 16.

C-1 HYDROXYLATION

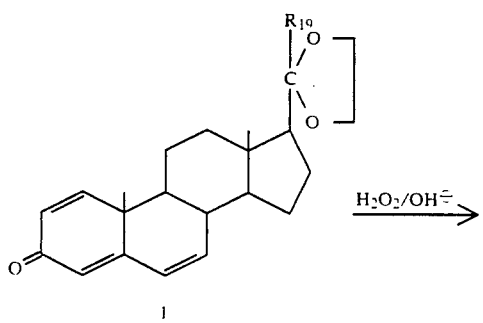

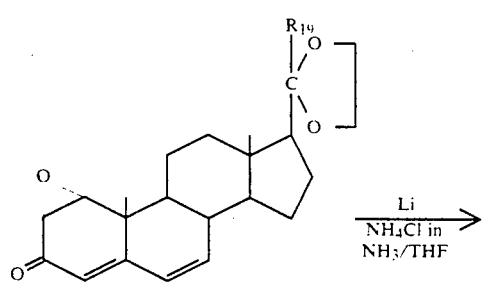

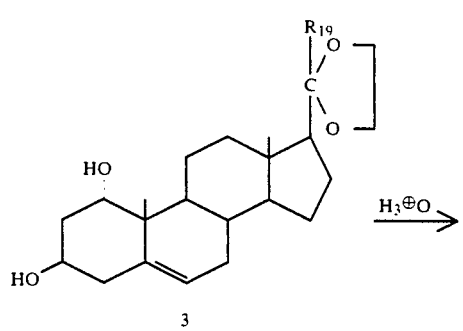

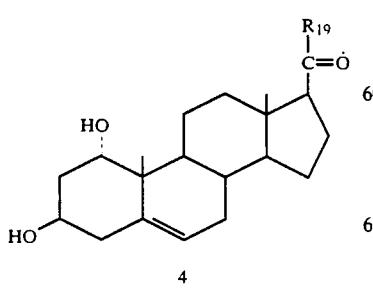

Alkaline hydrogen peroxide epoxidation of a compound of Formula I, such as pregna-1,4,6-triene-3,20-dione-20-ketal 1 with basic hydrogen peroxide yields the 1α,2α-epoxide 2. Treatment of 1α,2α-epoxypregna-4,6-dien-3,20-dione-20-ketal 2 with a large excess each of lithium metal and ammonium chloride in ammonia-tetrahydrofuran (1:1) under reflux leads to 1α,3β-dihydroxy-5-pregnen-20-one 20-ketal. Hydrolysis of the ketal affords 1α,3β-dihydroxy-5-pregnen-20-one (4).

C-2 Hydroxylation

2α,3β-dihydroxyandrost-5-en-17-one

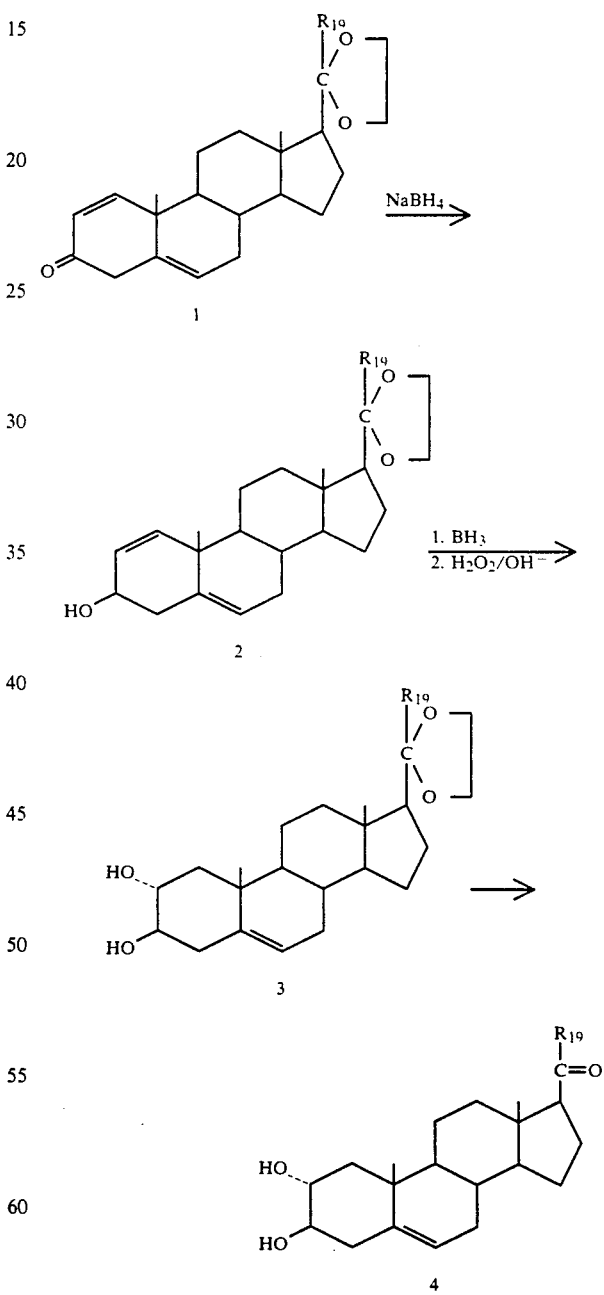

Reduction of pregna-1,5-dien-3,20-dione-20-ketal 1 with sodium borohydride yields 3β-hydroxy 1,5-pregnadien-20-one-20-ketal 2. Hydroxylation of the C-1 double bond by hydroboration followed by oxidation with alkaline hydrogen peroxide affords 2α,3β-dihydroxy-5-pregnen-17-one-17-ketal 3. Deprotection of the C-20 ketone with aqueous acid yields 2α,3β-dihydroxy-5-pregnene-17-one, 4.

Carbon-4 Hydroxylation

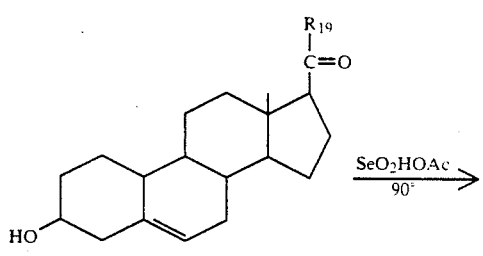

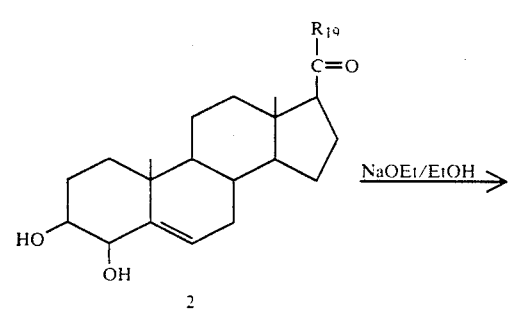

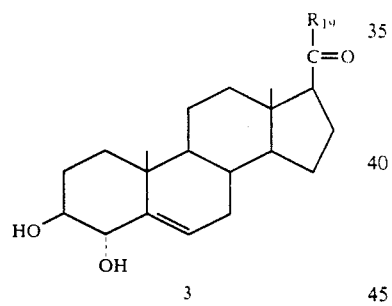

Selenium dioxide oxidation of 3β-hydroxy-5-pregnen-20-one yields 3β,4β-dihydroxy-5-pregnen-20-one 2. The axial C-4 alcohol may be epimerized to the equatorial position by reaction with sodium ethoxide in ethanol to yield 3β,4α-dihydroxy-5-pregnen-20-one, 3.

Carbon-7 Hydroxylation

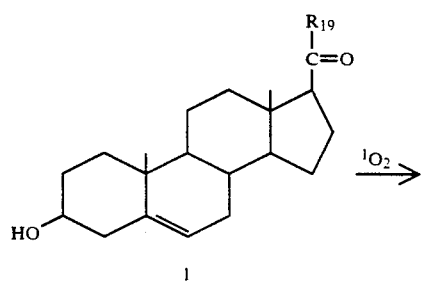

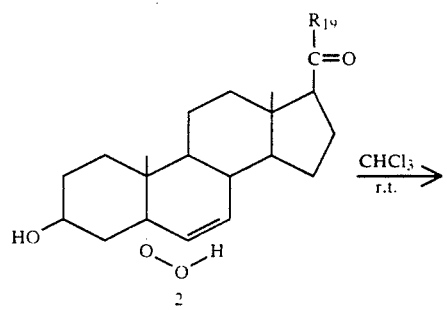

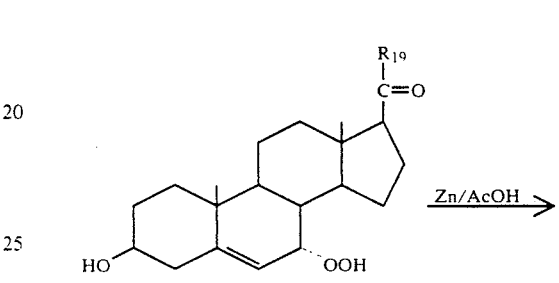

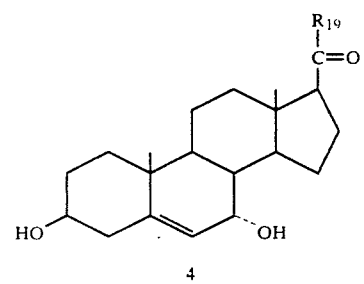

3β-Hydroxy-5-pregnen-20-one 1 reacts with singlet oxygen to yield 5α-hydroperoxy-3β-hydroxy-6-pregnene-20-one 2. This hydroperoxide undergoes a rearrangement when in chloroform solution to yield 7α-hydroperoxy-3β-hydroxy-5-pregnene-17-one, 3. Treatment of the hydroperoxide with zinc and acetic acid yields 3β,7α-dihydroxy-5-pregnen-20-one 4.

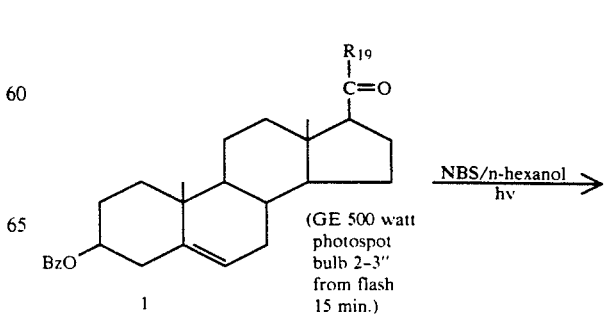

27

-continued

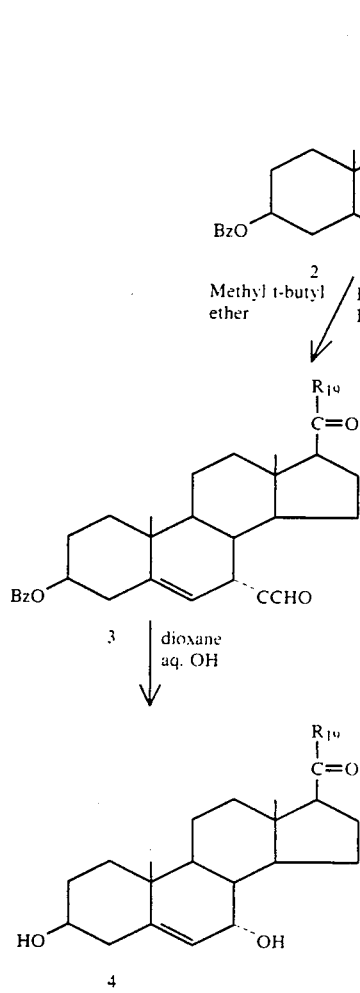

Alternatively, irradiation for approximately 15 minutes of 3β-benzyloxy-5-pregnen-20-one 1 in the presence of NBS produces the 7-αBromo-3β-benzyloxy-5-pregnen-20-one 2. The light source is provided by a G.E. 500 watt photospot bulb, which is placed 2-3" from the flask. Reaction of 2 with sodium formate in the presence of methyl 7-butyl ether produces the formate ester 3. Substitution with aqueous base, such as OH⁻, results in the 3,7-dihydroxy-5-pregnen-20-one 4.

Carbon-11 Hydroxylation

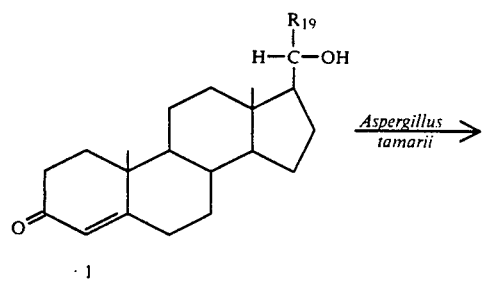

28

-continued

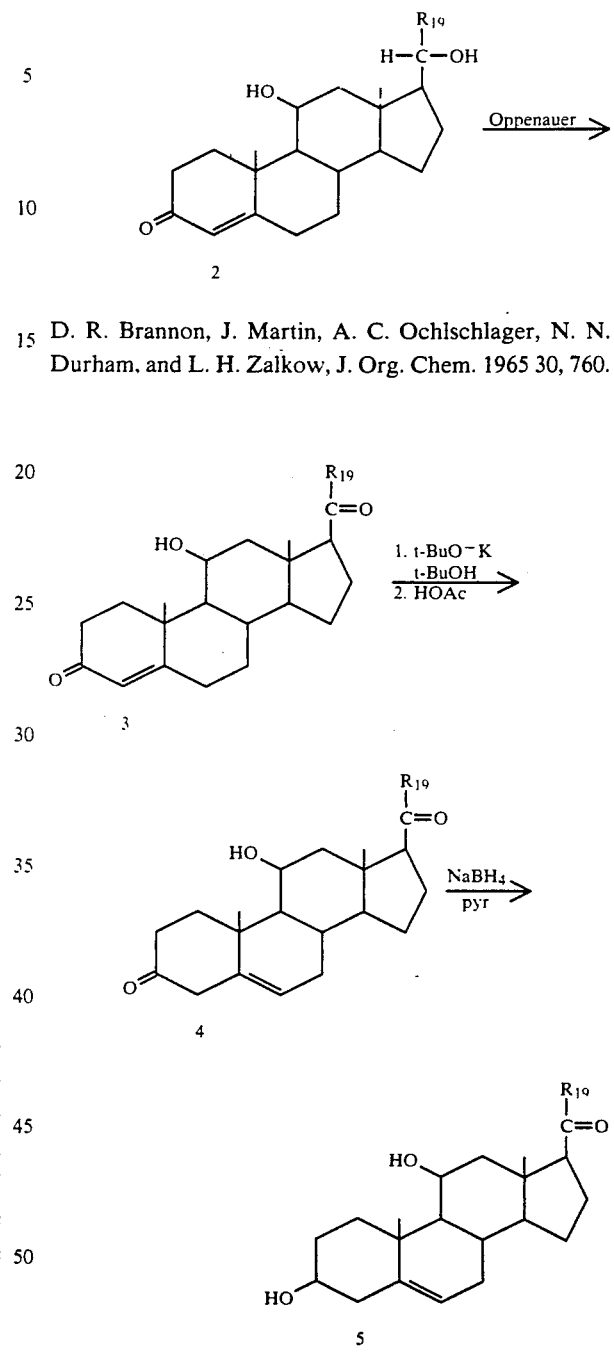

D. R. Brannon, J. Martin, A. C. Ochlschlager, N. N. Durham, and L. H. Zalkow, J. Org. Chem. 1965 30, 760.

Hydroxylation of 1, such as 20-hydroxy-5-pregnen-3-one, at Carbon-11 using *Aspergillus tamarii* affords 11β,20β-dihydroxy-5-pregnen-3-one 2. Oppenauer oxidation of 2 oxidizes the 20β-alcohol in the presence of the hindered 11β-hydroxyl group to yield 11β-hydroxy-5-pregnen-3,20-dione 3. Migration of the double bond out of conjunction by treatment with potassium t-butoxide followed by protonation with acetic acid yields 11β-hydroxy-5-pregnen-3,20-dione 4. Selective reduction of 4 yields 3β,11β-dihydroxy-5-pregnen-17-one 5.

Halogenation at Carbon-1

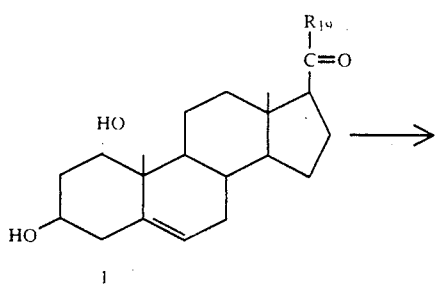

1

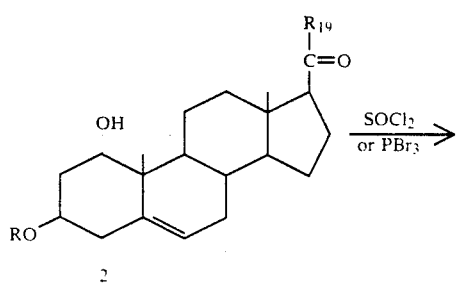

2

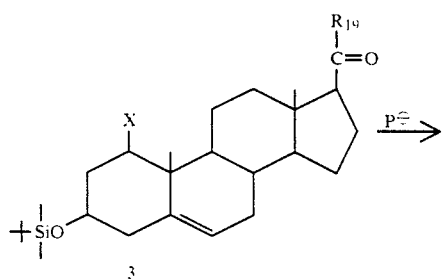

3

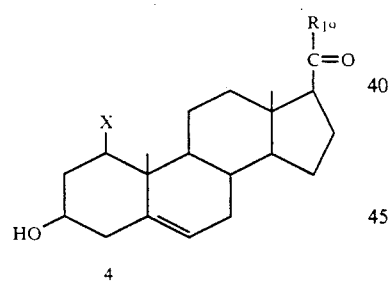

4

X = Cl, Br, I

Selective protection of the Carbon-3 hydroxyl in the presence of the 1α-hydroxyl group should yield 2. For example, 1α, -3β-dihydroxy-5-pregnen-20-one 1 reacts with t-butyl-dimethyl silyl chloride in the presence of imidazole using dimethylformamide as a solvent to yield 1α,3β-dihydroxy-5-pregnene-20-one 3t-butyl-dimethylsilyl ether, 2. Reaction of 2 with thionyl chloride, or phosphorous tribromide or catechol phosphochloridate followed by iodine yields the corresponding 1β-chloro, bromo or iodo derivatives 3. Reaction of 3 (R=Cl, Br, I) with tetrabutyl ammonium fluoride yields 1β-halo-3β-hydroxy-5-pregnen-17-one, 4 (R=Cl, Br or I). The fluoride (4, R=F) may be synthesized via a similar route using an ester as the protecting group at C-3 and reacting the 1α-hydroxyl group with diethyl (2-chloro-1,1,2-trifluoroethyl)amine. Hydrolysis should yield 1-β-fluoro-3β-hydroxy-5-pregnen-20-one, 4, R=F.

Halogenation at Carbon-2

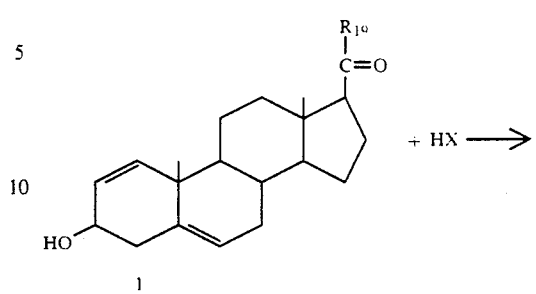

1

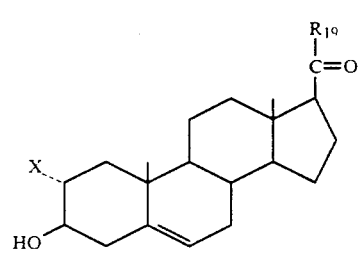

2

Addition of HX across the C-1 double bond in 3β-hydroxy-1,5-pregnadien-20-one, 1, yields a mixture of the C-1 and C-2 haloenated steroids. Separation affords 2-halo-3β-hydroxy-5-pregnen-20-one (2, R=F, Cl, Br, I).

Halogenation at Carbon-3

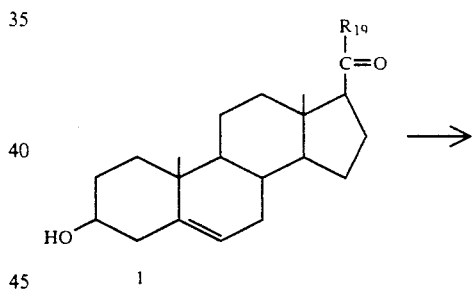

1

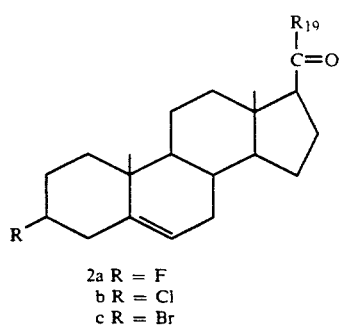

2a R = F
b R = Cl
c R = Br
d R = I

Reaction of 3β-hydroxy-5-pregnen-20-one 1 with diethyl (2-chloro-1,1,2-trifluoroethyl) amine yields 3β-fluoro-5-pregnen-20-one 1. Reaction of 1 with thionyl chloride yields 3β-chloro-5-pregnen-20-one. Reaction of 1 with phosphorus tribromide yields 3β-bromo-5-pregnen-17-one, 2c. Reaction of 1 with catechol phosphochloridate followed by iodine yields 3β-iodo-5-pregnen-17-one 2d.

Halogenation at Carbon-4

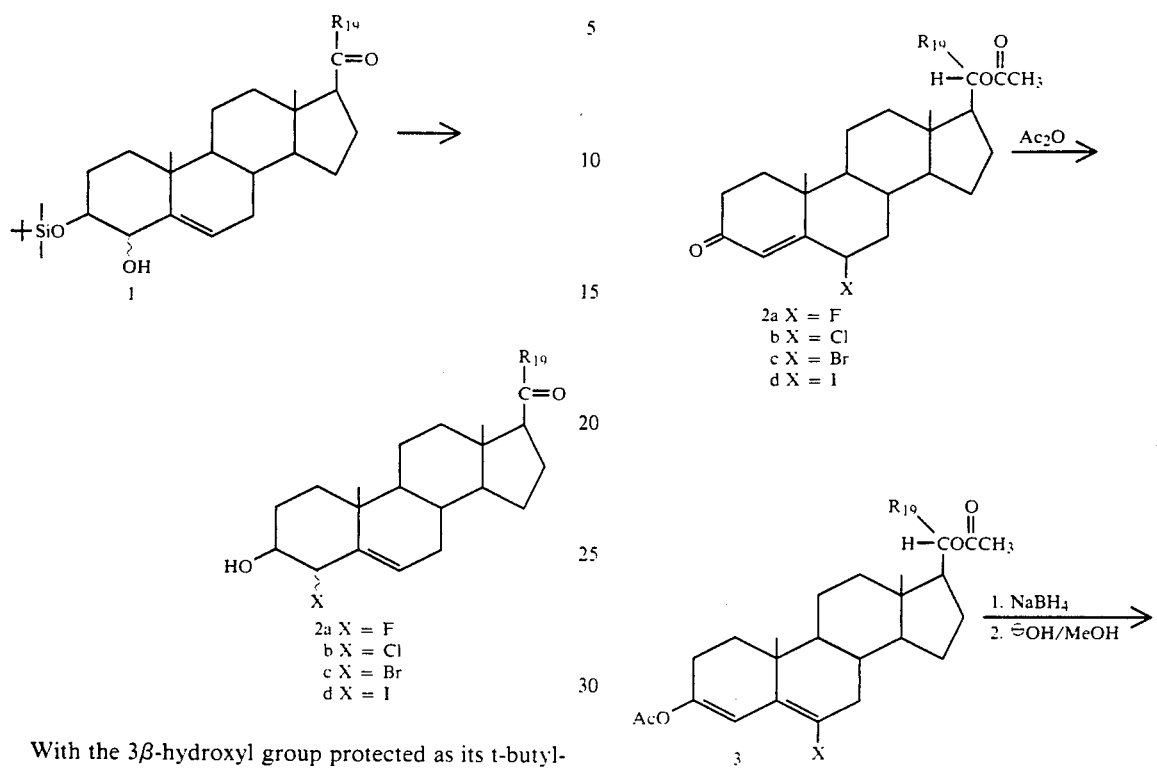

2a X = F
b X = Cl
c X = Br
d X = I

With the 3β-hydroxyl group protected as its t-butyldimethylsilyl ether the C-4 hydroxyl may be chlorinated using thionyl chloride. Treatment with fluoride ion cleaves the silyl ether to yield 4ξchloro-3β-hydroxy-5-pregnen-20-one 2b. Reaction of 3,4-dihydroxy-5-pregnen-20-one 3-t-butyldimethylsilyl ether 1 with O-phenylene phosphochloridite, followed by displacement with bromide ion and cleavage of the silyl ether with fluoride ion yields 4ξbromo-3β-hydroxy-5-pregnen-20-one 2c. Reaction of 1 with catechol phosphochloridate, followed by iodine and cleavage of the silyl ether with fluoride yields 4ξiodo-3β-hydroxy-5-pregnen-20-one 2d. Fluorination of 3β,4ξdihydroxy-5-pregnen-20-one-3-acetate with diethyl (2-chloro-1,1,2-trifluoroethyl) amine followed by hydrolysis of the ester yields 4ξfluoro-3β-hydroxy-5-pregnen-20-one 2a.

Halogenation at Carbon-6

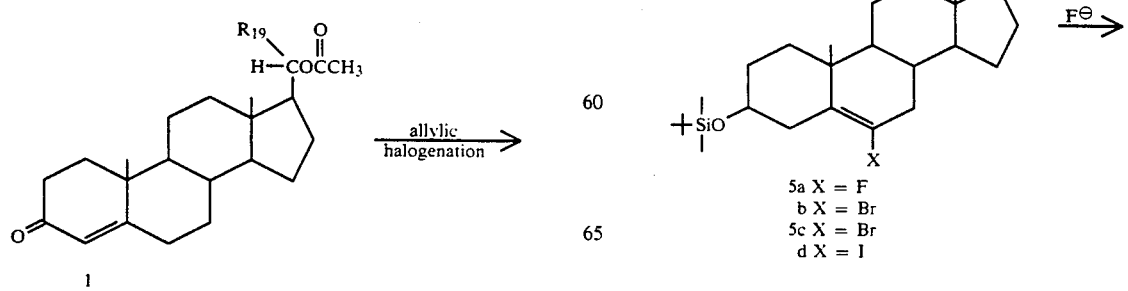

5a X = F
b X = Br
5c X = Br
d X = I

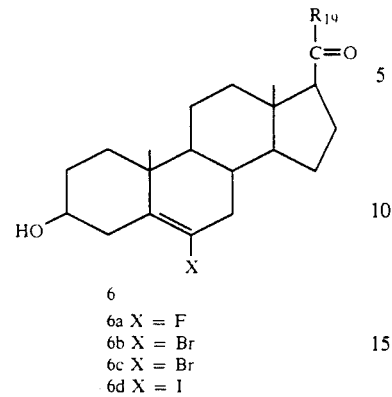

6
6a X = F
6b X = Br
6c X = Br
6d X = I

Allylic bromination of 20β-hydroxy-4-pregnen-3-one 20-acetate 1 using N-bromosuccinimide together with a radical initiator such as light or benzoyl peroxides or aliphatic azo compounds [RR'C(CN)—N=N—C(CN)RR'] e.g. azobisisobutyronitrile yields 6β-bromo-20β-hydroxy-4-pregnen-3-one-20-acetate 2. Allylic chlorination of 1 using sulfuryl chloride together with a radical initiator such as light or benzoyl peroxide or aliphatic azo compound yields 6β-chloro-20β-hydroxy-4-pregnen-3-one-20-acetate, 2c. Allylic iodination of 1 using mercuric iodide and light yields 6β-iodo-20β-hydroxy-4-pregnen-3-one-20-acetate, 2d. Acetylation of 2 with acetic anhydride and p-toluene sulfonic acid in toluene yields 6-halo-3, 20β-dihydroxy 3,5-pregnadien-3,20-diacetate 3. Sodium borohydride reduction of 3 followed by basic hydrolysis of the C-20 acetate yields 6-halo-5-pregnen-3β,20β-diol, 4. Selective protection of the C-3 hydroxyl group as its t-butyldimethylsilyl ether followed by chromium trioxide oxidation of the C-20 hydroxyl group yields 6-halo-3β-hydroxy-5-pregnen-20-one 3-t-butyldimethylsilyl ether 5. Treatment of 5 with fluoride ion yields 6-halo-3β-hydroxy-5-pregnen-20-one 6. The C-6 fluoro analogue may be synthesized from the C-6 bromo diacetate, 3c, by treatment with silver fluoride. Following the above sequence, reaction of 6-fluoro-3,20β-dihydroxy 3,5-pregnadien-3,20-diacetate, 3a with sodium borohydride yields 6-fluoro-3β-hydroxy-5-pregnen-20-one, 6a.

Halogenation at Carbon-7

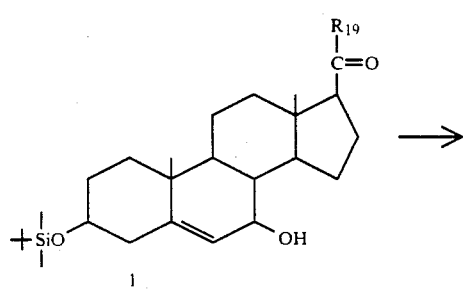

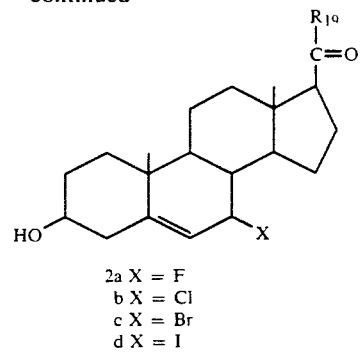

2a X = F
b X = Cl
c X = Br
d X = I

Reaction of 3β,7-dihydroxy-5-pregnen-20-one-3-t-butyldimethylsilyl ether 1 with thionyl chloride yields the C-7 chloro-steroid. Deprotection of the 3β-hydroxyl group affords 7-chloro-3β-hydroxy-5-pregnen-20-one, 2b. Reaction of 1 with catechol phosphochloridate followed by displacement with bromide ion and deprotection yields 7-bromo-3β-hydroxy-5-pregnen-20-one, 2c. Similarly reaction of 1 with catechol phosphochloridate followed by displacement with iodine and deprotection yields 7-iodo-3β-hydroxy-5-pregnen-20-one, 2d. Fluorination of 3β,7-dihydroxy-5-pregnen-20-one 3-acetate with diethyl (2-chloro-1,1,2-trifluoro-ethyl) amine followed by hydrolysis of the ester yields 7-fluoro-3β-hydroxy-5-pregnen-20-one, 2a.

Halogenation at Carbon-9

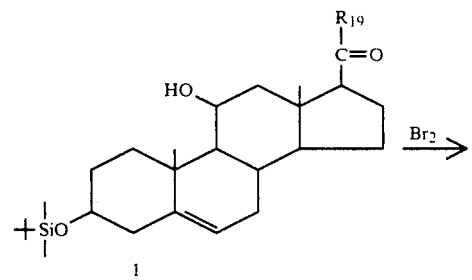

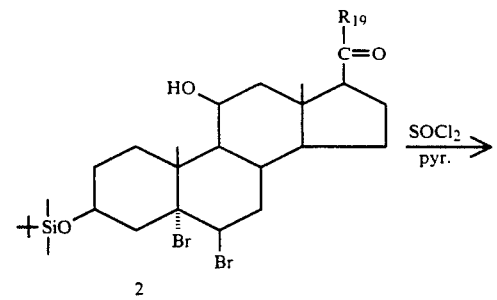

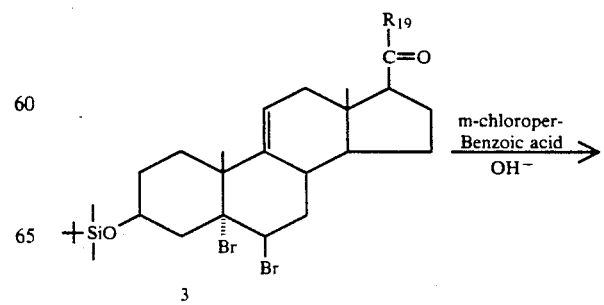

Halogenation at Carbon-11

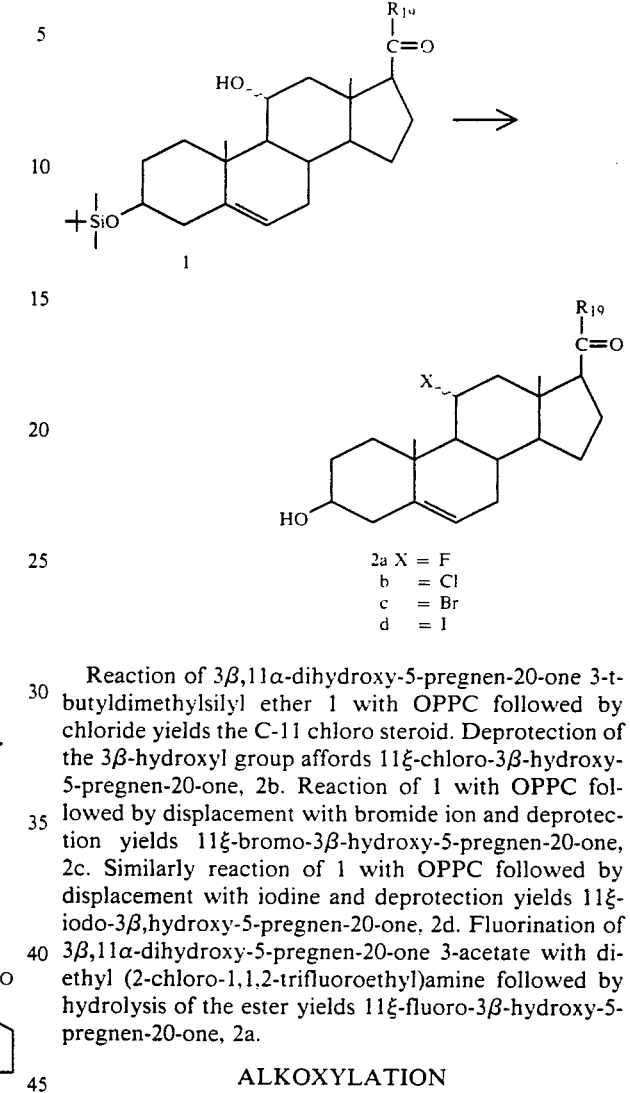

2a X = F
 b   = Cl
 c   = Br
 d   = I

Reaction of 3β,11α-dihydroxy-5-pregnen-20-one 3-t-butyldimethylsilyl ether 1 with OPPC followed by chloride yields the C-11 chloro steroid. Deprotection of the 3β-hydroxyl group affords 11ξ-chloro-3β-hydroxy-5-pregnen-20-one, 2b. Reaction of 1 with OPPC followed by displacement with bromide ion and deprotection yields 11ξ-bromo-3β-hydroxy-5-pregnen-20-one, 2c. Similarly reaction of 1 with OPPC followed by displacement with iodine and deprotection yields 11ξ-iodo-3β,hydroxy-5-pregnen-20-one, 2d. Fluorination of 3β,11α-dihydroxy-5-pregnen-20-one 3-acetate with diethyl (2-chloro-1,1,2-trifluoroethyl)amine followed by hydrolysis of the ester yields 11ξ-fluoro-3β-hydroxy-5-pregnen-20-one, 2a.

ALKOXYLATION

The alkoxy groups are derived from the corresponding alcohols. The methoxy substituent for example is formed by reacting the corresponding alcohol in methylene chloride with boron trifluride and etheral diazomethane according to the procedure of Caserio, et al., JACS, 80, 2584 (1958). Similarly, the ethoxy substituent is formed by reacting the corresponding alcohol in methylene chloride with boron trifluoride and etheral diazoethane, generated in situ. Alternatively, the alkoxy substituents can also be added to the steroid ring by reacting the alcohol under Williamson reaction conditions with RX, where X is an organic leaving group such as halide tosylate or mesylate and R is loweralkyl. Any base normally employed to deprotonate an alcohol may be used, such as sodium hydride, sodium amide, sodium sodium hydroxide, triethylamino or disopropyl ethylamine. Reaction temperatures are in the range of −78° C. to reflux. The reaction is carried out in a solvent that will dissolve both reactants and is inert to both reactants and products as well. Solvents include, but are not limited to, diethyl ether, tetrahydrofuran, N,N-dimethylformamide, methylene chloride, and the like.

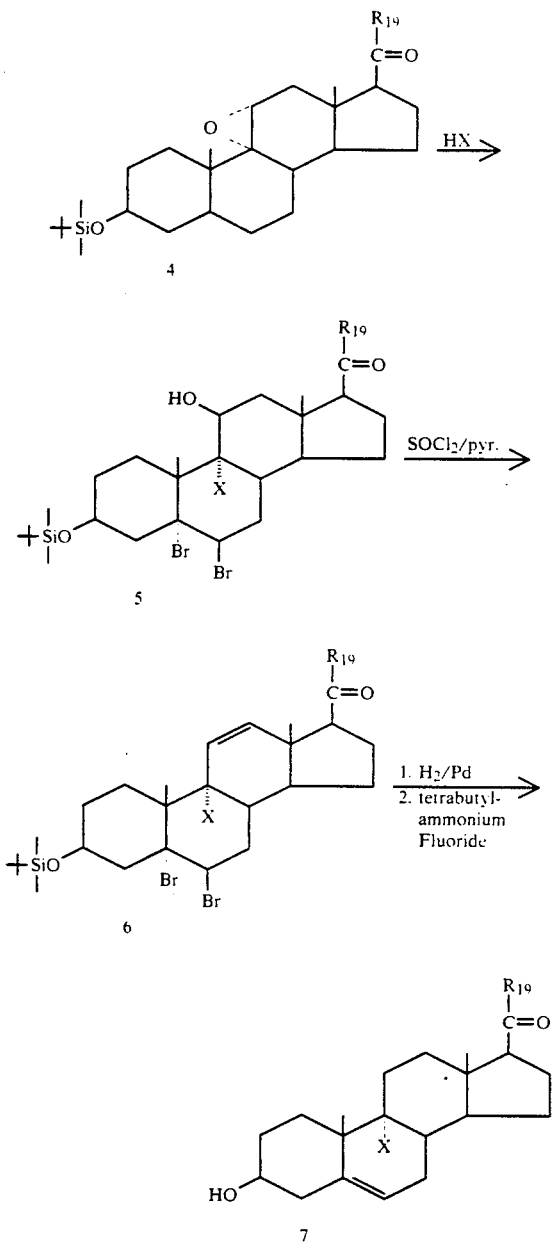

Bromination of 3β,11α-dihydroxy-5-pregnen-20-one 3-t-butyldimethylsilyl ether 1 yields the dibromide 2. Reaction of 2 with thionyl chloride produces the unsaturated compound, 3β-hydroxy-5,6-dibromo-9(11)-pregnen-20-one-3-t-butyl-dimethylsilyl ether 3. 3 is epoxidized with perbenzoic acid forming 4. Reaction of 4 with hydrohalic acid, such as HCl, HBr, forms the 9α-halo derivative 5. Dehydration of 5 with thionyl chloride produces the unsaturated compound, the 3β-hydroxy-5,6-dibromo-11-pregnen-20-one-3-t-butyl-dimethylsilyl ether 6. Catalytic hydrogenation of 6 followed by removal of the protecting group forms the 3-βhydroxy-9-α-halo-5-pregnen-20-one.

The ketone should be protected with protecting groups known in the art. Examples of many of the possible protecting groups that may be utilized are found in "Protective Groups in Organic Synthesis," by T. W. Green, John Wiley and Sons, 1981. For example, the ketone may be protected as the ethyleneketal.

The following examples further illustrate the invention:

EXAMPLE I

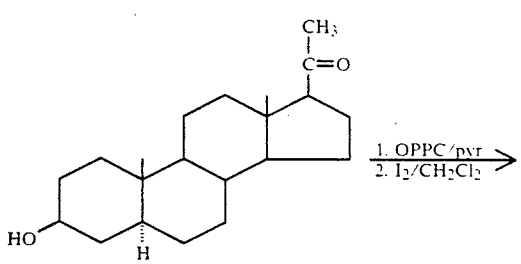

1

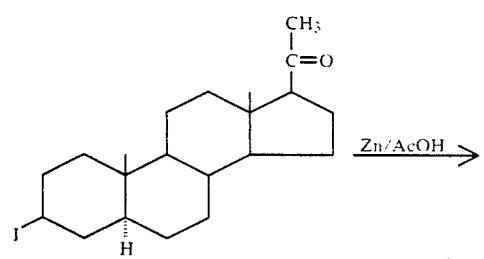

2

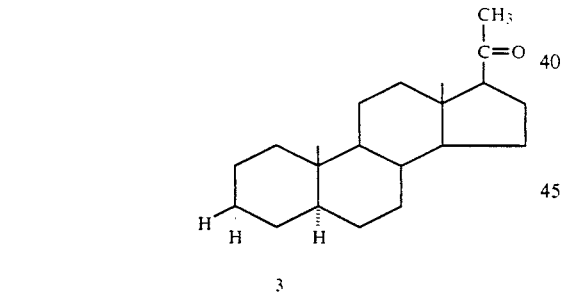

3

5α-Pregnan-20-one (3)

Treatment of a methylene chloride solution of 3β-hydroxy-5α-pregnan-20-one with equivalent amounts of O-phenylenephosphorochloridite and pyridine for 2 hours at room temperature affords the phosphite ester at C-3. Decomposition of the phosphite ester was accomplished by addition of an equivalent amount of elemental iodine. The organic product is washed with dilute NaOH, followed by water and filtered with anhydrous sodium sulfate and 3β-iodo-5-α-pregnan-20-one (2) was isolated.

Refluxing 2 in acetic acid with zinc for 30 minutes provides the deiodination product 5α-pregnan-20-one (3).

Similarly, using the appropriate starting materials, the following compounds are also prepared:

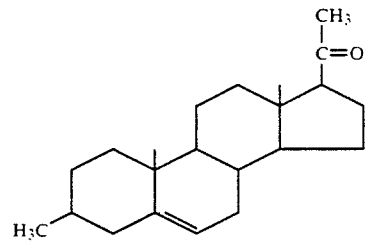

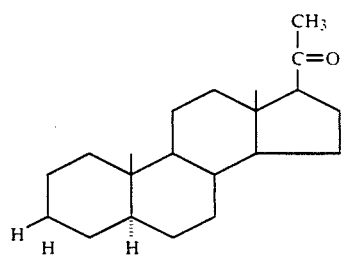

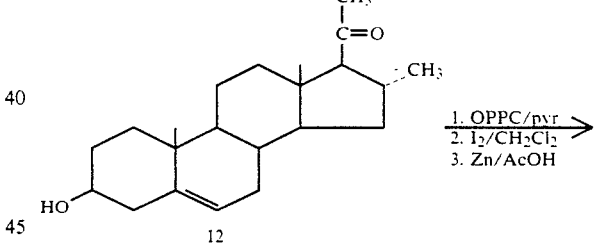

EXAMPLE II

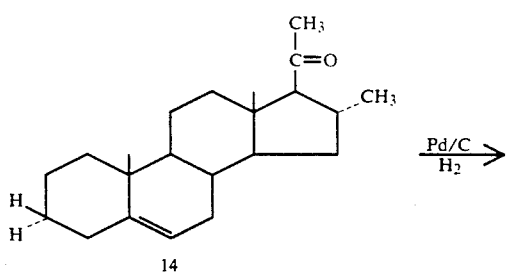

12

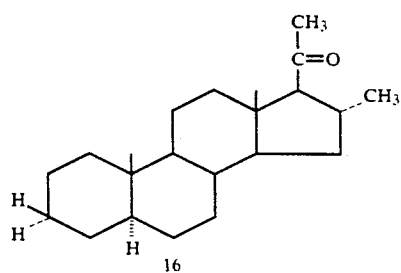

14

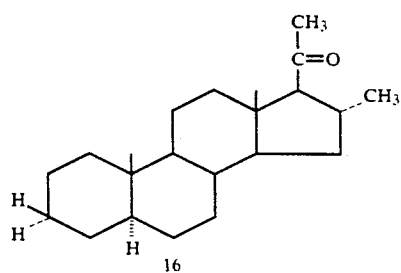

16

-continued

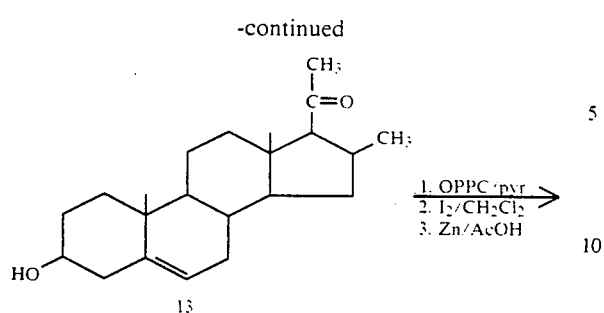

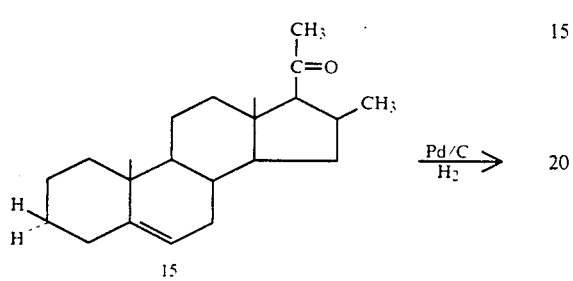

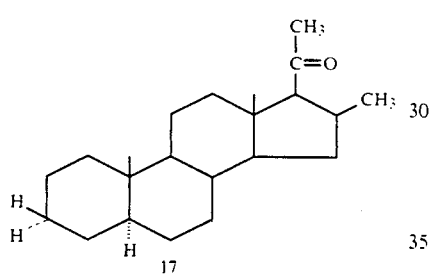

16α-Methyl-5-pregnen-20-one (14).
16α-Methyl-5α-pregnan-20-one (16).
16β-Methyl-5-pregnen-20-one (15), and
16β-Methyl-5α-pregnan-20-one (17)

Reductive removal of the C-3 oxygen atoms from 12 and 13 via the 3α-iodides proceeds by the usual reaction sequence, affording the 16α-methyl and 16β-methyl pregnenes 14 and 15. Catalytic hydrogenation with Pd/C in ethanol provides the corresponding 5α-pregnanes 16 and 17.

EXAMPLE III

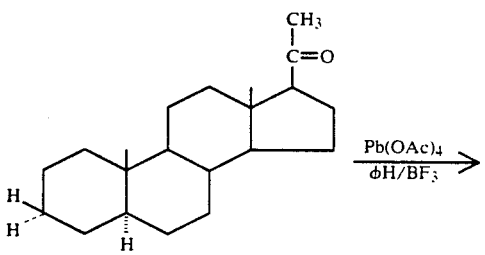

-continued

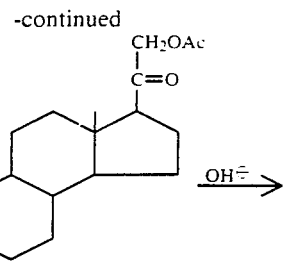

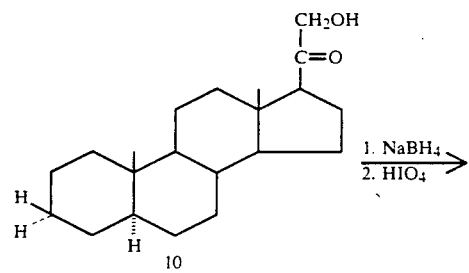

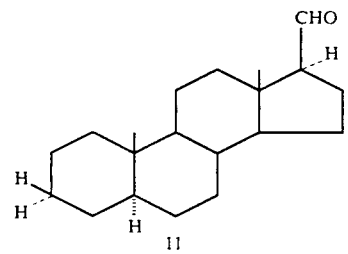

17β-Formyl-5α-androstane (11)

Treatment of 5α-pregnan-20-one (3) in benzene with lead tetraacetate and boron trifluoride at room temperature gives the ketol acetate 9. Deacetylation of 9 in methanol with a catalytic amount of sodium hydroxide supplies the free α-ketol 10. Sequential treatment of 10 with sodium borohydride (giving primarily the 20β-glycol) and one equivalent of periodic acid furnishes 17β-formyl-5α-androstane (11).

EXAMPLE IV

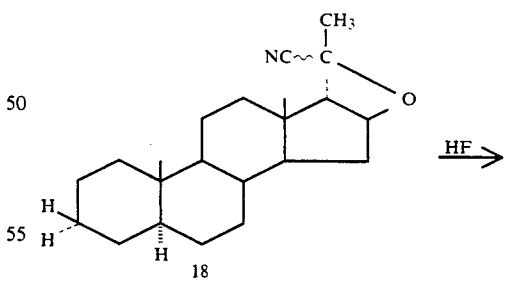

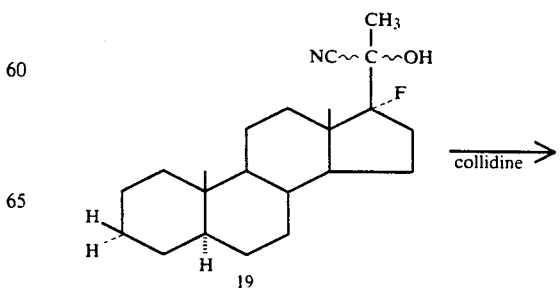

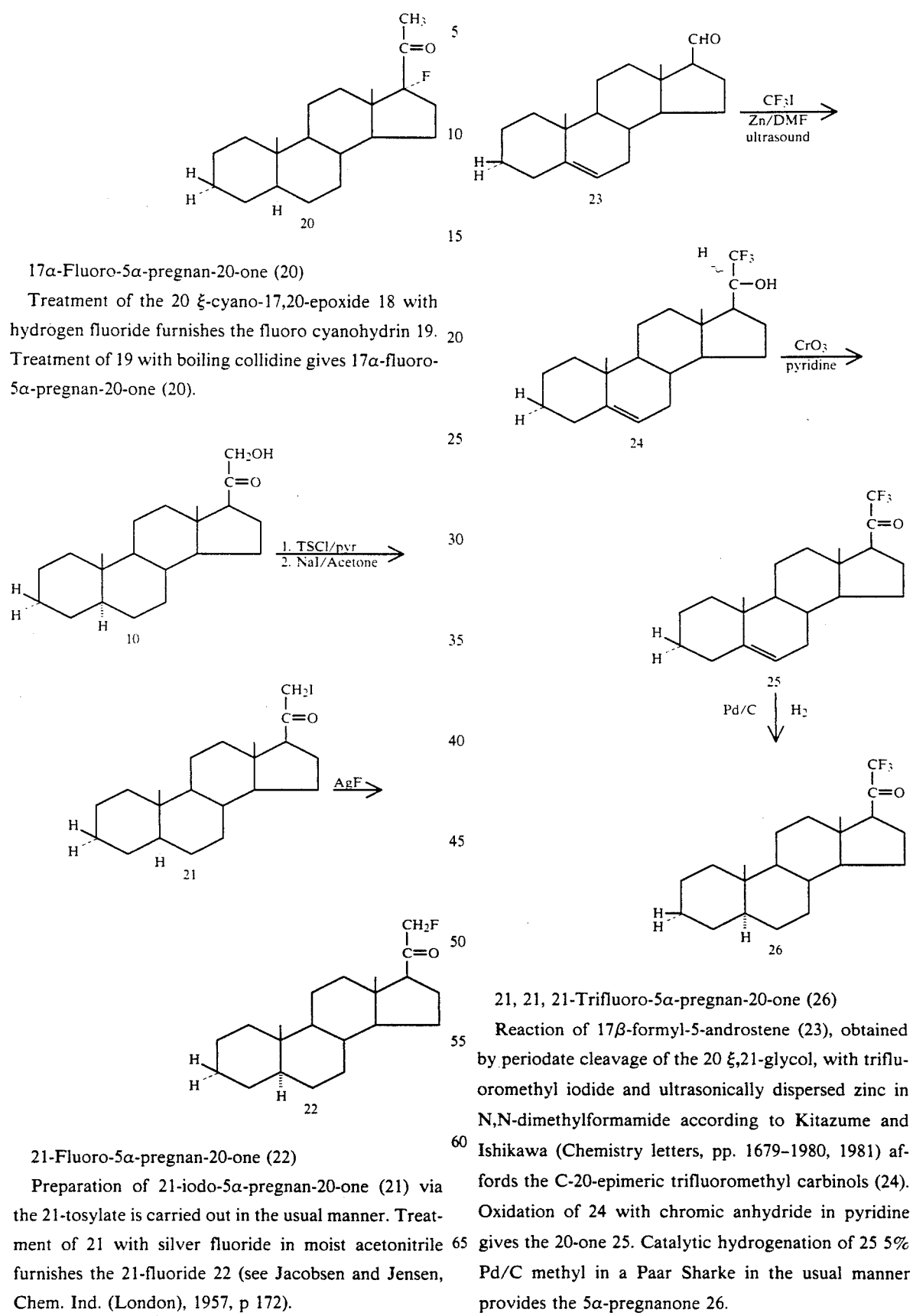

17α-Fluoro-5α-pregnan-20-one (20)

Treatment of the 20 ξ-cyano-17,20-epoxide 18 with hydrogen fluoride furnishes the fluoro cyanohydrin 19. Treatment of 19 with boiling collidine gives 17α-fluoro-5α-pregnan-20-one (20).

21-Fluoro-5α-pregnan-20-one (22)

Preparation of 21-iodo-5α-pregnan-20-one (21) via the 21-tosylate is carried out in the usual manner. Treatment of 21 with silver fluoride in moist acetonitrile furnishes the 21-fluoride 22 (see Jacobsen and Jensen, Chem. Ind. (London), 1957, p 172).

EXAMPLE V

21, 21, 21-Trifluoro-5α-pregnan-20-one (26)

Reaction of 17β-formyl-5-androstene (23), obtained by periodate cleavage of the 20 ξ,21-glycol, with trifluoromethyl iodide and ultrasonically dispersed zinc in N,N-dimethylformamide according to Kitazume and Ishikawa (Chemistry letters, pp. 1679–1980, 1981) affords the C-20-epimeric trifluoromethyl carbinols (24). Oxidation of 24 with chromic anhydride in pyridine gives the 20-one 25. Catalytic hydrogenation of 25 5% Pd/C methyl in a Paar Sharke in the usual manner provides the 5α-pregnanone 26.

EXAMPLE VI

Preparation of 17α-Methyl-5-pregnen-20-one by Favorsky Rearrangement

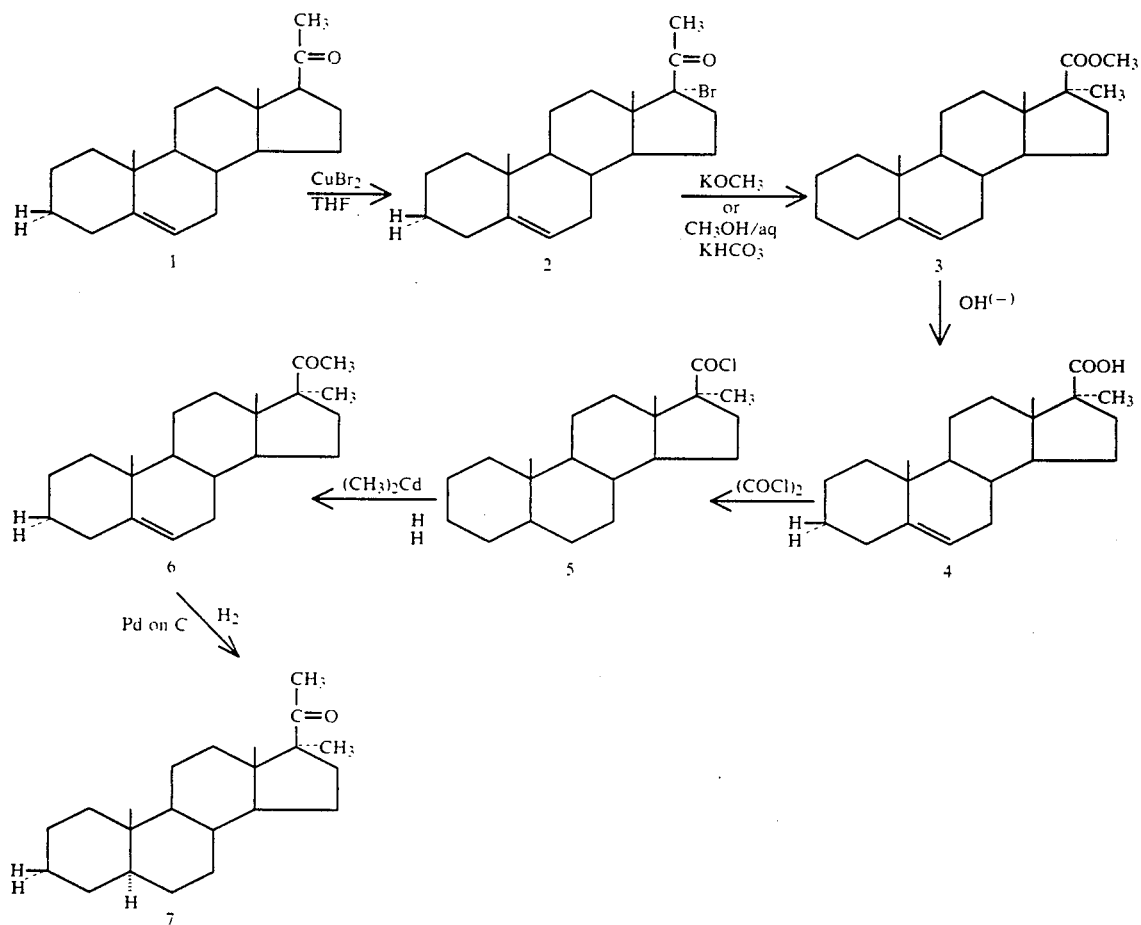

bicarbonate[3] brings about Favorsky rearrangement to the methyl 17α-methyl etienate 3.

[2] Plattner et al., Helv. 32, 270 (1949)
[3] R. E. Marker and R. B. Wagner JACS 64, 216 (1942)

17α-Methyl-5-Pregnen-20-one (6) via 3, 4, and 5

17α-Bromo-5-Pregnen-20-one (2) from 1

Refluxing a solution of 10 mmoles of 5-pregnen-20-one, 1, (available from pregnenolone via zinc/acetic acid or the 3β-iodide) in tetrahydrofuran (150 ml) with cupric bromide (20 mmoles) for one hour affords the 17α-bromide 2 in high yield.[1]

[1] F. R. Glazier. J. Org. Chem. 27, 4397 (1962)

Ethyl 17α-Methyl-5-etiocholenoate (3) from 2

Refluxing 17α-bromo-5-pregnen-20-one with potassium methoxide[2] or aqueous methanolic potassium bicarbonate[3] brings about Favorsky rearrangement to the methyl 17α-methyl etienate 3.

Treatment of the 17α-methyl methyl etienate with alkali furnishes the acid 4 which is converted to the acyl chloride 5 with oxalylchloride. Treatment of 5 with dimethyl cadmium supplies the 17α-Methyl pregenone 6. Hydrogenation of 6 gives 7, 17α-Methyl-5α-pregnan-20-one.

EXAMPLE VII

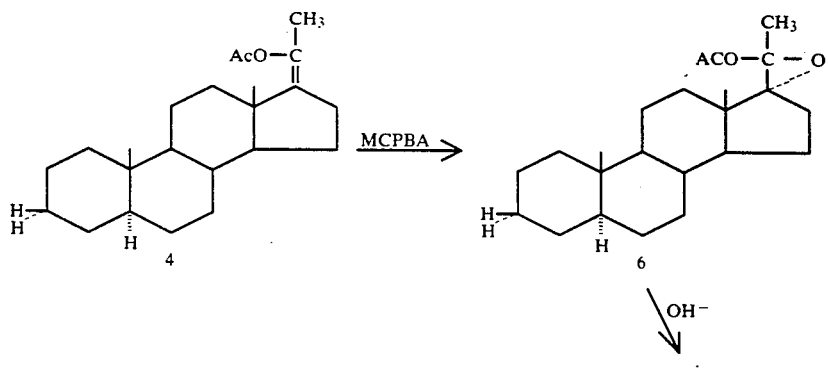

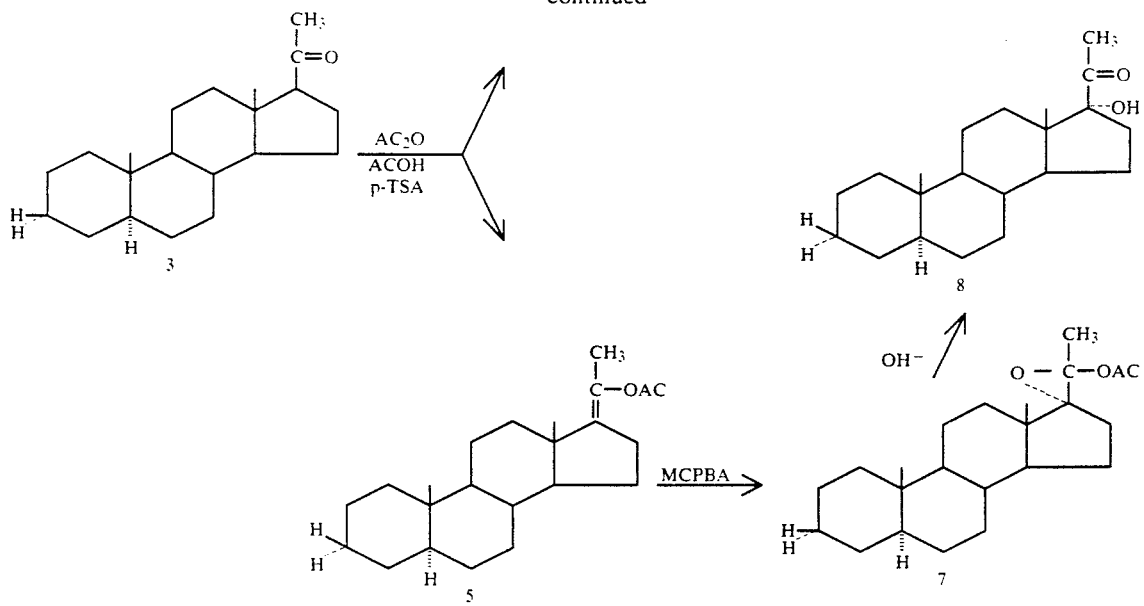

20 Acetoxy-cis-17(20)-5α-pregnene(4),
20-Acetoxy-trans-17(20)-5α-pregnene(5), and
17α-hydroxy-5α-pregnan-20-one(8)

Reaction of 5α-pregnan-20-one (3) with a mixture of acetic anhydride, acetic acid, and p-toluene sulfonic acid followed by HPLC of the crude product affords the isomeric enol acetates 4 and 5. Epoxidation of 4 and 5 in benzene with m-chloro perbenzoic acid overnight at room temperature furnishes the epoxy acetates 6 and 7. Saponification of both 6 and 7 with methanolic sodium hydroxide gives 17α-hydroxy-5α-pregnan-20-one (8) as a common product.

EXAMPLE VIII

Using the procedures described hereinabove and the appropriate starting materials, the following

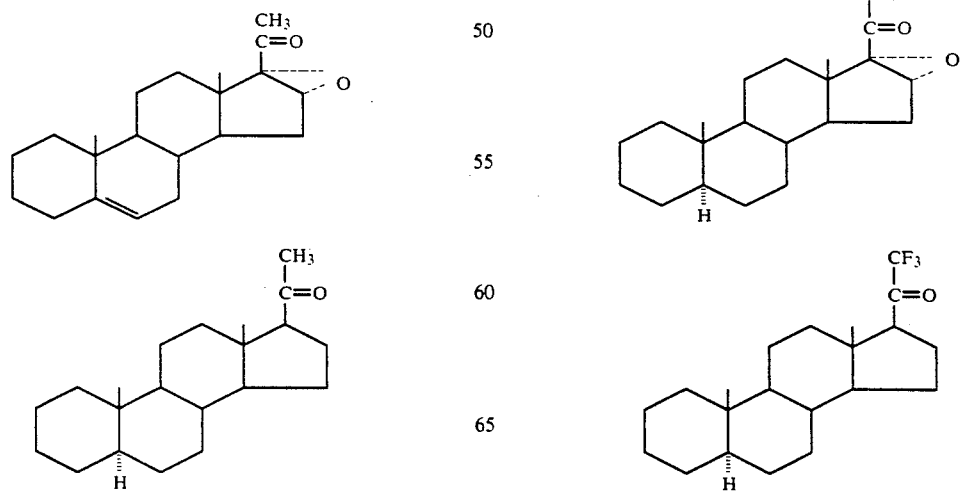

47
-continued
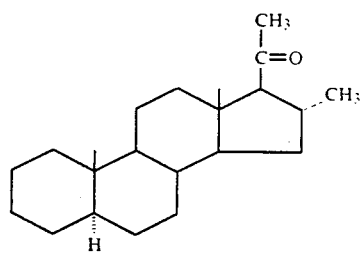
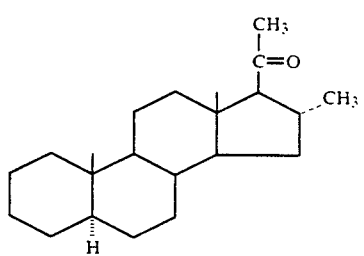
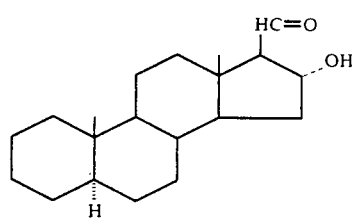
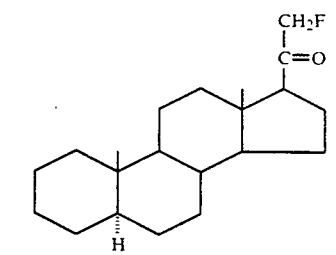
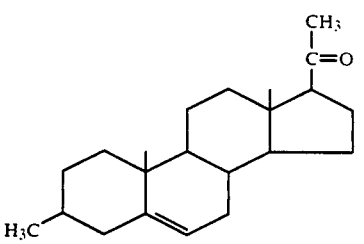
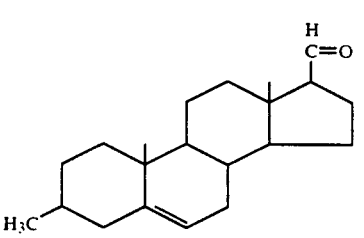
48
-continued
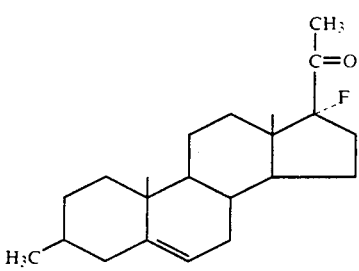
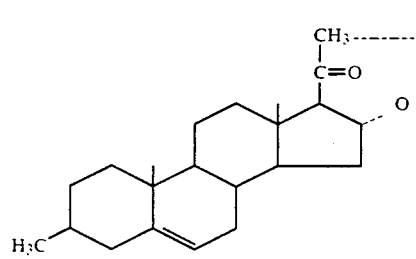
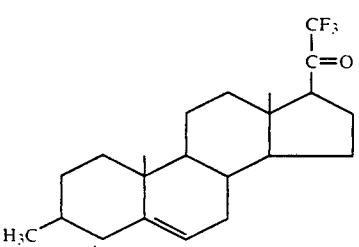
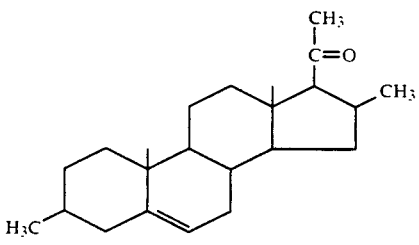
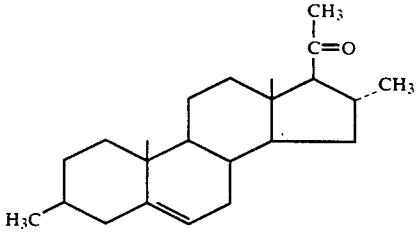
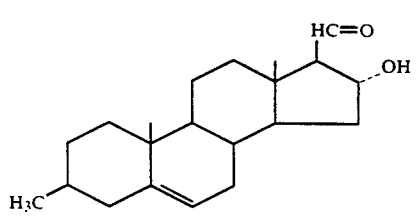

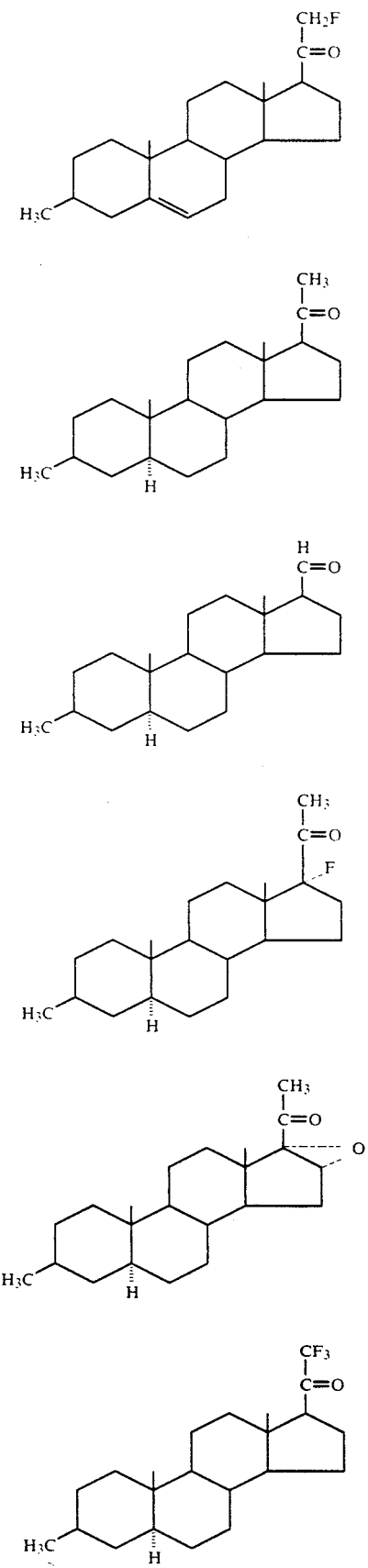
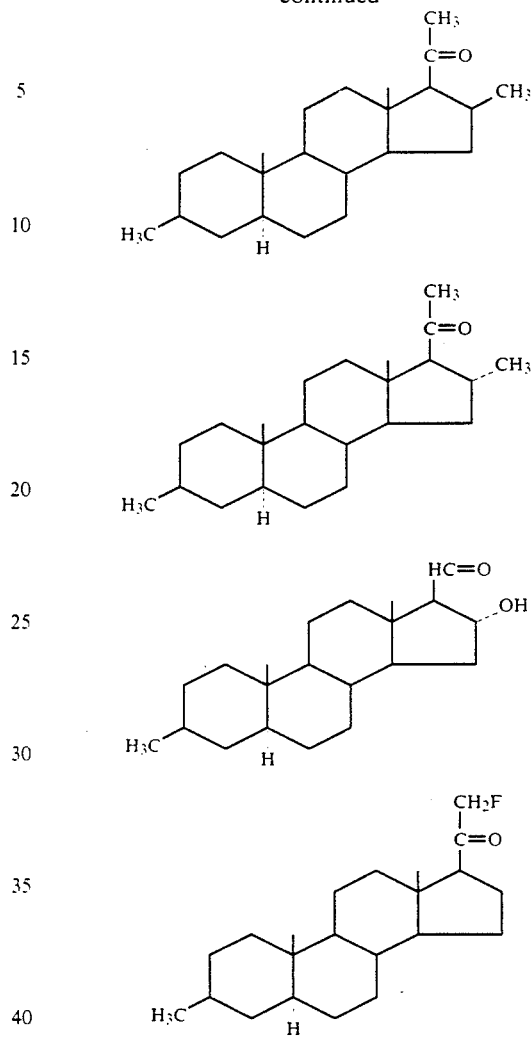

Compounds of the present invention are also effective anti-obesity agents. In fact, the compounds wherein the B ring of the steroid contains a double bond in the 5, 6 position are more effective anti-obesity agents than the saturated counterpart, which has some effectiveness in the obesity test.

The compounds of the present invention are also effective anti-hyperglycemic agents, anti-hypercholesterolemic agents, and anti-atherosclerotic. Moreover, the compounds of the present invention are effective anti-auto-immune agents, and are effective in the prophylasis and treatment of auto-immune diseases such as lupus erythematosis and Coomb's positive hemolytic anemia.

The compounds of the present invention do not possess the side effects that are exhibited by other steroids. Unlike other steroids such as DHEA, the compounds of the present invention do not exhibit an estrogen effect. Furthermore, the compounds of the present invention do not exhibit liver enlargement, which is prevalent with other steroids, such as DHEA.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. For parental administration they may be used in the form of a sterile solution containing other solutes, for example, enough saline or glucose to make the solution isotomic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages, substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with those other therapeutic agents.

When given orally, the therapeutic doses of the compounds of the present invention are generally in the range of from about 4 to about 450 mg/kg/day depending upon the particular mammalian host and the particular effect desired, e.g. anti-obesity, anti-diabetes, etc. When given parenterally, the compounds are administered generally in dosages of, for example, 0.5 to about 15 mg/kg/day, also depending upon the host and effect desired.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Obviously, other modifications and variations of the present invention are possible in light of the above teachings. It is, therefore, to be understood that changes may be made in the particular embodiments of this invention which are within the full intended scope of the invention as defined by the appended claims.

What is claimed is:

1. A pharmaceutical composition comprising a pharmaceutical effective amount of a compound and a pharmaceutical carrier therefor, wherein the compound has the formula:

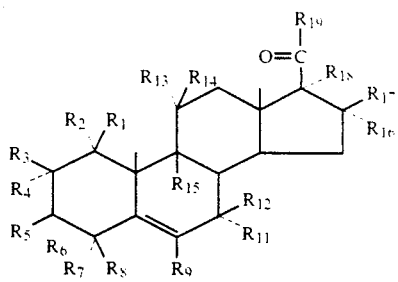

wherein $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;

$R_5$ and $R_6$ are independently hydrogen or lower alkyl;

$R_9$ is hydrogen, lower alkyl or halogen;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, dihaloloweralkyl or mono-haloloweralkyl.

2. The composition according to claim 1, wherein lower alkyl and lower alkoxy groups contain 1-3 carbon atoms.

3. The composition according to claim 1, wherein lower alkyl is methyl.

4. The composition according to claim 1, wherein halogen is fluorine.

5. The composition according to claim 1, wherein $R_5$ is hydrogen or methyl and $R_6$ is hydrogen.

6. The composition according to claim 1, wherein at most one of $R_1$, $R_2$, $R_3$, $R_4$, $R_7$, $R_8$, $R_9$, $R_{11}$, $R_{12}$, $R_{13}$, $R_{14}$ or $R_{15}$ is other than hydrogen.

7. The composition according to claim 1, wherein $R_1$, $R_2$, $R_3$, $R_4$, $R_7$, $R_8$, $R_9$, $R_{11}$, $R_{12}$, $R_{13}$, $R_{14}$ or $R_{15}$ are hydrogen.

8. The composition according to claim 1, wherein $R_{19}$ is hydrogen, trifluoromethyl, difluoromethyl or monofluoromethyl or methyl.

9. The composition according to claim 1, wherein $R_{18}$ is hydrogen or fluorine, $R_{16}$ is hydrogen, fluorine or methyl or $R_{16}$ and $R_{18}$ taken together with the carbon to which they are attached form an epoxide ring and $R_{17}$ is hydrogen or methyl.

10. The composition according to claim 1 wherein the compound has the formula:

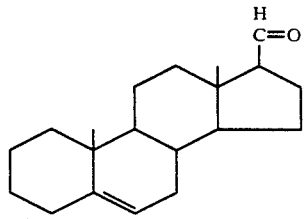

11. The composition according to claim 1 wherein the compound has the formula:

12. The composition according to claim 1 wherein the compound has the formula:

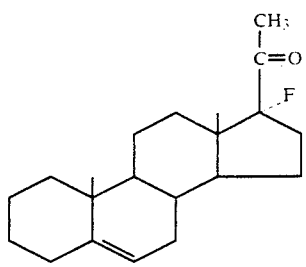

13. The composition according to claim 1 wherein the compound has the formula:

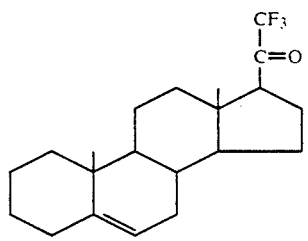

14. The composition according to claim 1 wherein the compound has the formula:

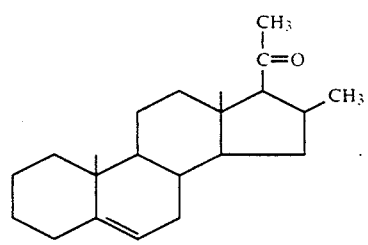

15. The composition according to claim 1 wherein the compound has the formula:

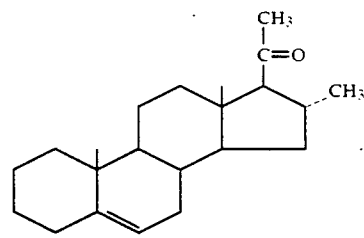

16. The composition according to claim 1 wherein the compound has the formula:

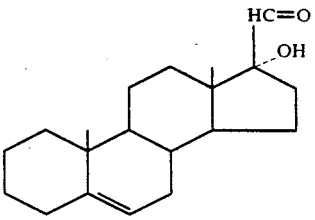

17. The composition according to claim 1 wherein the compound has the formula:

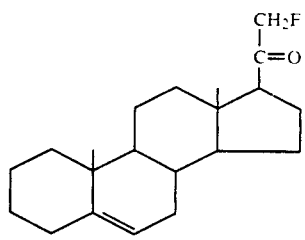

18. The composition according to claim 1 wherein the compound has the formula:

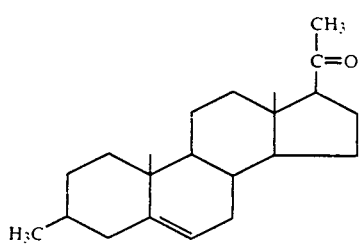

19. The composition according to claim 1 wherein the compound has the formula:

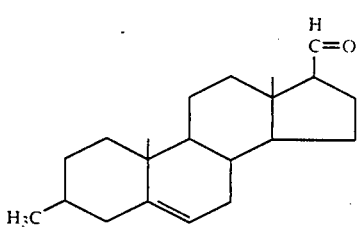

20. The composition according to claim 1 wherein the compound has the formula:

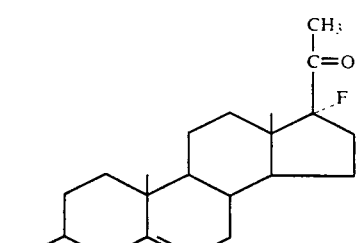

21. The composition according to claim 1 wherein the compound has the formula:

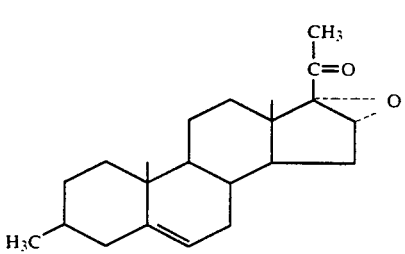

22. The composition according to claim 1 wherein the compound has the formula:

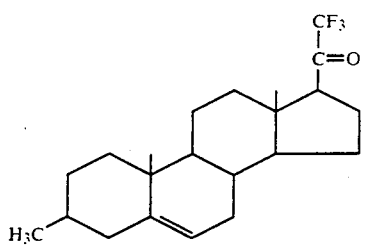

23. The composition according to claim 1 wherein the compound has the formula:

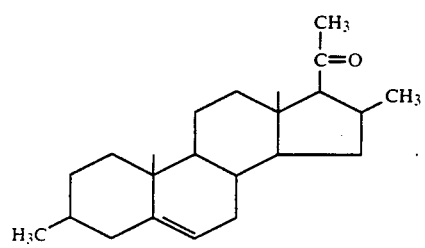

24. The composition according to claim 1 wherein the compound has the formula:

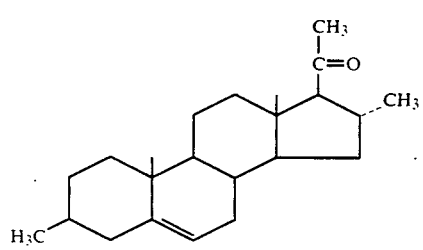

25. The composition according to claim 1 wherein the compound has the formula:

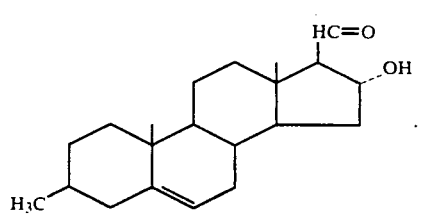

26. The composition according to claim 1 in which the compound has the formula:

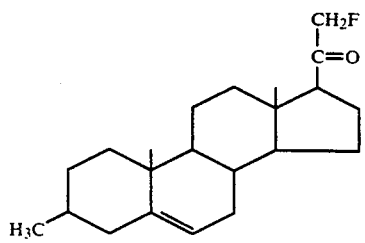

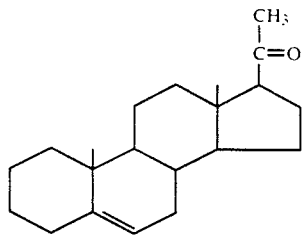

27. The composition according to claim 1 in which the compound has the formula:

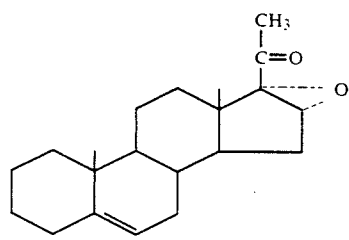

28. A method for the prophylaxis of obesity in an animal which comprises administering to said animal an anti-obesity affective amount of a compound according to claim 1.

29. A pharmaceutical composition comprising a pharmaceutically effective amount of a compound and a pharmaceutical carrier therefor, said compound having the formula:

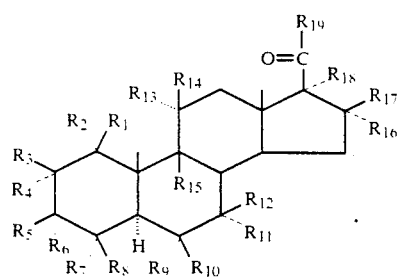

wherein
$R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;
$R_5$ and $R_6$ are independently hydrogen or lower alkyl;
$R_9$ and $R_{10}$ are each independently hydrogen, lower alkyl or halogen;
$R_{16}$ and $R_{17}$ are independently hydrogen, lower alkyl, halogen, hydroxy or lower alkoxy;
$R_{18}$ is hydrogen, lower alkyl, halogen or lower alkoxy; or
$R_{16}$ and $R_{18}$ taken together with the carbon to which they are attached form an epoxide ring; and
$R_{19}$ is hydrogen, lower alkyl, tri-haloloweralkyl, di-haloloweralkyl or mono-haloloweralkyl.

30. The composition according to claim 29 wherein lower alkyl and lower alkoxy groups contain 1-3 carbon atoms.

31. The composition according to claim 29 wherein lower alkyl is methyl.

32. The composition according to claim 29 wherein halogen is fluorine.

33. The composition according to claim 29 wherein $R_5$ is hydrogen or methyl and $R_6$ is hydrogen.

34. The composition according to claim 29 wherein at most one of $R_1$, $R_2$, $R_3$, $R_4$, $R_7$, $R_8$, $R_9$, $R_{10}$, $R_{11}$, $R_{12}$, $R_{13}$, $R_{14}$ or $R_{15}$ are other than hydrogen.

35. The composition according to claim 29 wherein $R_1$, $R_2$, $R_3$, $R_4$, $R_7$, $R_8$, $R_9$, $R_{10}$, $R_{11}$, $R_{12}$, $R_{13}$, $R_{14}$ or $R_{15}$ are hydrogen.

36. The composition according to claim 29 wherein $R_{19}$ is hydrogen, trifluoromethyl, difluoromethyl or monofluoromethyl or methyl.

37. The composition according to claim 29 wherein $R_{18}$ is hydrogen or fluorine, $R_{16}$ is hydrogen, fluorine or methyl or $R_{16}$ and $R_{18}$ taken together with the carbon to which they are attached form an epoxide ring and $R_{17}$ is hydrogen or methyl.

38. The composition according to claim 29 wherein the compound has the formula:

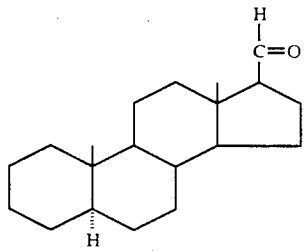

39. The composition according to claim 29 wherein the compound has the formula:

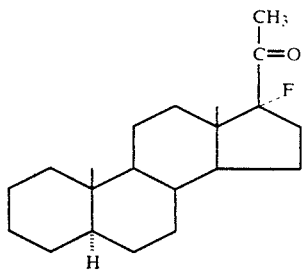

40. The composition according to claim 29 wherein the compound has the formula:

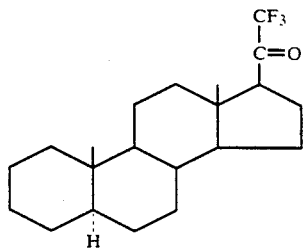

41. The composition according to claim 29 wherein the compound has the formula:

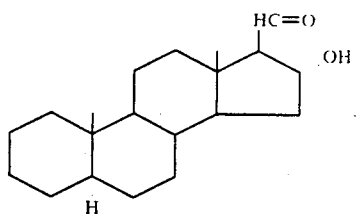

42. The composition according to claim 29 wherein the compound has the formula:

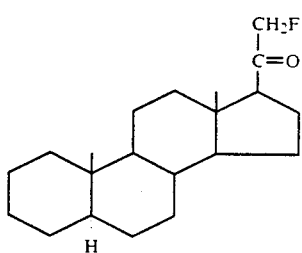

43. The composition according to claim 29 wherein the compound has the formula:

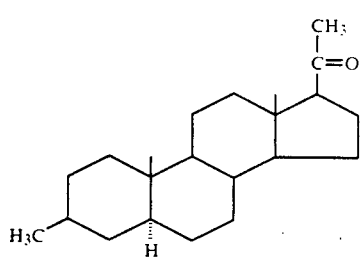

44. The composition according to claim 29 wherein the compound has the formula:

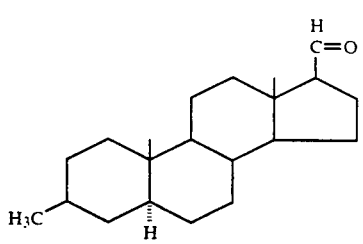

45. The composition according to claim 29 wherein the compound has the formula:

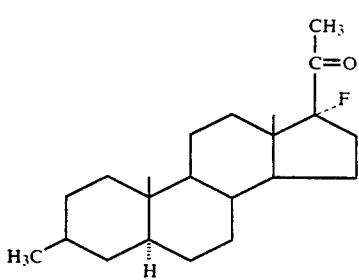

46. The composition according to claim 29 wherein the compound has

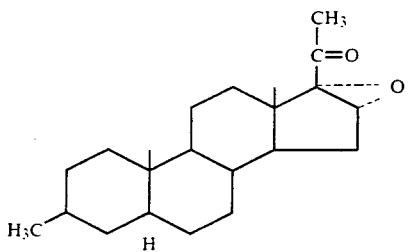

47. The composition according to claim 29 wherein the compound has the formula:

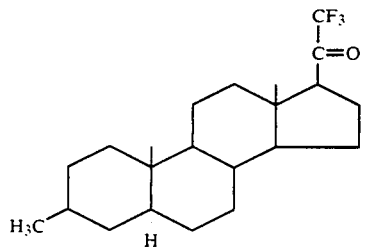

48. The composition according to claim 29 wherein the compound has the formula:

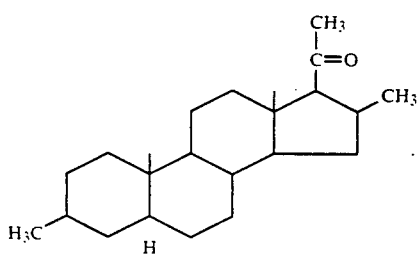

49. The composition according to claim 29 wherein the compound has the formula:

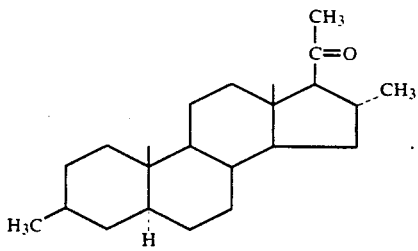

50. The composition according to claim 29 wherein the compound has the formula:

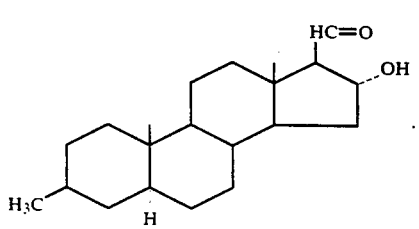

51. The composition according to claim 29 wherein the compound has the formula:

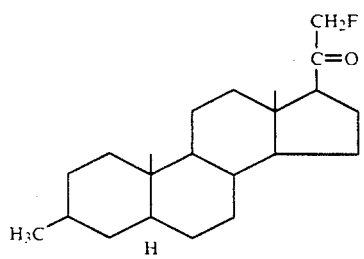

52. The composition according to claim 29 in which the compound has the formula:

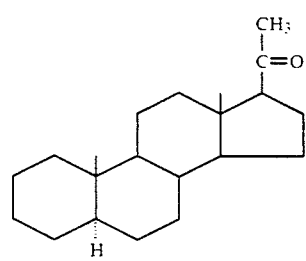

53. The composition according to claim 29 where the compound has the formula:

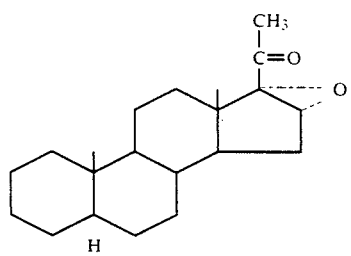

54. The composition according to claim 29 wherein the compound has the formula:

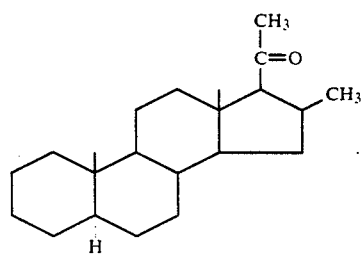

55. The composition according to claim 29 wherein the compound has the formula:

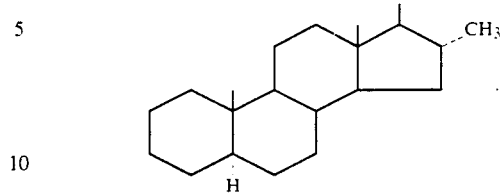

56. A method for the prophylaxis of obesity in an animal which comprises administering to said animal an anti-obesity effective amount of a compound according to claim 29.

57. A pharmaceutical composition comprising a pharmaceutically effective amount of a compound and a pharmaceutical carrier therefor, said compound having the formula:

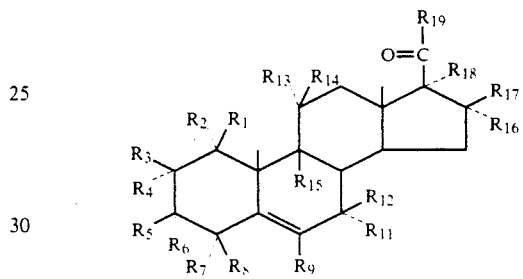

wherein
$R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;
$R_5$ and $R_6$ are independently hydrogen or methyl;
$R_9$ is hydrogen, lower alkyl or halogen;
$R_{16}$ and $R_{17}$ are independently hydrogen, lower alkyl, halogen, hydroxy or lower alkoxy;
$R_{18}$ is hydrogen, lower alkyl, halogen or lower alkoxy; or
$R_{16}$ and $R_{18}$ taken together with the carbon to which they are attached form an epoxide ring; and
$R_{19}$ is hydrogen, lower alkyl, tri-haloloweralkyl, di-haloloweralkyl or mono-haloloweralkyl.

58. The composition according to claim 57, wherein lower alkyl and lower alkoxy groups contain 1–3 carbon atoms.

59. The composition according to claim 57, wherein lower alkyl is methyl.

60. The composition according to claim 57, wherein halogen is fluorine.

61. The composition according to claim 57, wherein $R_5$ is hydrogen or methyl and $R_6$ is hydrogen.

62. The composition according to claim 57, wherein at most one of $R_1$, $R_2$, $R_3$, $R_4$, $R_7$, $R_8$, $R_9$, $R_{11}$, $R_{12}$, $R_{13}$, $R_{14}$ or $R_{15}$ is other than hydrogen.

63. The composition according to claim 57, wherein $R_1$, $R_2$, $R_3$, $R_4$, $R_7$, $R_8$, $R_9$, $R_{11}$, $R_{12}$, $R_{13}$, $R_{14}$ or $R_{15}$ are hydrogen.

64. The composition according to claim 57, wherein $R_{19}$ is hydrogen, trifluoromethyl, difluoromethyl or monofluoromethyl or methyl.

65. The composition according to claim 57, wherein $R_{18}$ is hydrogen or fluorine, $R_{16}$ is hydrogen, fluorine or methyl or $R_{16}$ and $R_{18}$ taken together with the carbon to which they are attached form an epoxide ring and $R_{17}$ is hydrogen or methyl.

66. A pharmaceutical composition comprising a pharmaceutically effective amount of a compound and a pharmaceutical carrier therefor, said compound having the formula:

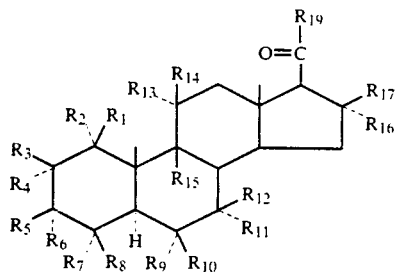

wherein $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;

$R_5$ and $R_6$ are independently hydrogen or methyl;

$R_9$ and $R_{10}$ are each independently hydrogen, lower alkyl or halogen;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

67. The composition according to claim 66, wherein lower alkyl and lower alkoxy groups contain 1-3 carbon atoms.

68. The composition according to claim 66, wherein lower alkyl is methyl.

69. The composition according to claim 66, wherein halogen is fluorine.

70. The composition according to claim 66, wherein $R_5$ is hydrogen or methyl and $R_6$ is hydrogen.

71. The composition according to claim 66, wherein at most one of $R_1$, $R_2$, $R_3$, $R_4$, $R_7$, $R_8$, $R_9$, $R_{10}$, $R_{11}$, $R_{12}$, $R_{13}$, $R_{14}$ or $R_{15}$ are other than hydrogen.

72. The composition according to claim 66, wherein $R_1$, $R_2$, $R_3$, $R_4$, $R_7$, $R_8$, $R_9$, $R_{10}$, $R_{11}$, $R_{12}$, $R_{13}$, $R_{14}$ or $R_{15}$ are hydrogen.

73. The composition according to claim 66, wherein $R_{19}$ is hydrogen, trifluoromethyl, difluoromethyl or mono-fluoromethyl or methyl.

74. The composition according to claim 66, wherein $R_{18}$ is hydrogen or fluorine, $R_{16}$ is hydrogen, fluorine or methyl or $R_{16}$ and $R_{18}$ taken together with the carbon to which they are attached form an epoxide ring and $R_{17}$ is hydrogen or methyl.

75. A pharmaceutical composition comprising a pharmaceutically effective amount of a compound and a pharmaceutical carrier therefor, said compound having the formula:

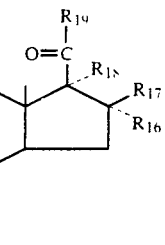

wherein $R_5$ and $R_6$ are independently hydrogen or lower alkyl;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form a epoxide ring; and $R_{19}$ is hydrogen, lower alkyl, tri-haloloweralkyl, di-haloloweralkyl or mono-haloloweralkyl.

76. The composition according to claim 75 wherein lower alkyl group contains 1-3 carbon atoms.

77. The composition according to claim 75 wherein lower alkyl is methyl.

78. The composition according to claim 75 wherein halogen is fluorine.

79. The composition according to claim 75 wherein $R_{19}$ is hydrogen, trifluoromethyl, difluoromethyl or mono-fluoromethyl or methyl.

80. The composition according to claim 75 wherein $R_{18}$ is hydrogen or fluorine, $R_{16}$ is hydrogen, fluorine or methyl or $R_{16}$ and $R_{18}$ taken together with the carbon to which they are attached form an epoxide ring and $R_{17}$ is hydrogen or methyl.

81. The composition according to claim 75, in which the compound has the formula:

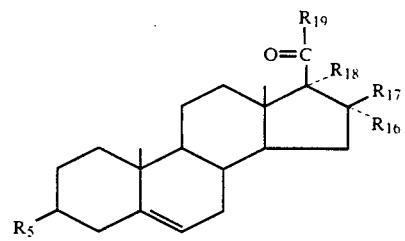

wherein $R_5$ is hydrogen or lower alkyl;

$R_{16}$ and $R_{17}$ are independently hydrogen, lower alkyl, halogen, hydroxy or lower alkoxy; or $R_{18}$ is hydrogen, lower alkyl, halogen or lower alkoxy;

$R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

82. The composition according to claim 81, wherein lower alkyl group contains 1-3 carbon atoms.

83. The composition according to claim 81, wherein lower alkyl is methyl.

84. The composition according to claim 81, wherein halogen is fluorine.

85. The composition according to claim 81, wherein $R_{19}$ is hydrogen, trifluoromethyl, difluoromethyl or mono-fluoromethyl or methyl.

86. The composition according to claim 81, wherein $R_{18}$ is hydrogen or fluorine, $R_{16}$ is hydrogen, fluorine or methyl or $R_{16}$ and $R_{18}$ taken together with the carbon to which they are attached form an epoxide ring and $R_{17}$ is hydrogen or methyl.

87. A pharmaceutical composition comprising a pharmaceutically effective amount of a compound and a pharmaceutical carrier therefor, said compound having the formula:

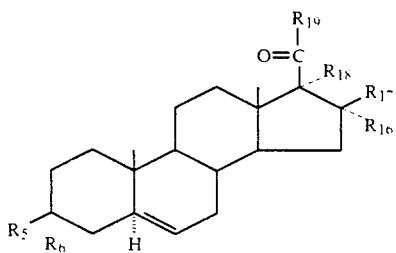

wherein $R_5$ and $R_6$ are independently hydrogen or lower alkyl;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

88. The composition according to claim 87, wherein lower alkyl group contains 1-3 carbon atoms.

89. The composition according to claim 87, wherein lower alkyl is methyl.

90. The composition according to claim 87, wherein halogen is fluorine.

91. The composition according to claim 87, wherein $R_{19}$ is hydrogen, trifluoromethyl, difluoromethyl or mono-fluoromethyl or methyl.

92. The composition according to claim 87, wherein $R_{18}$ is hydrogen or fluorine, $R_{16}$ is hydrogen, fluorine or methyl or $R_{16}$ and $R_{18}$ taken together with the carbon to which they are attached form an epoxide ring and $R_{17}$ is hydrogen or methyl.

93. The composition according to claim 87, which has the formula:

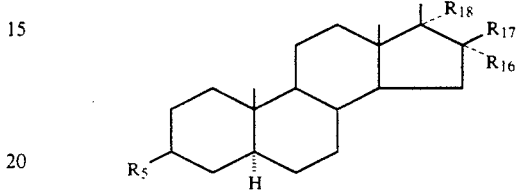

wherein $R_5$ is hydrogen or lower alkyl;

$R_{16}$ and $R_{17}$ are independently hydrogen, lower alkyl, halogen, hydroxy or lower alkoxy;

$R_{18}$ is hydrogen, lower alkyl, halogen or lower alkoxy; or $R_{16}$ and $R_{18}$ taken together with the carbon to which they are attached form an epoxide ring; and $R_{19}$ is hydrogen, lower alkyl, tri-haloloweralkyl, di-haloloweralkyl or mono-haloloweralkyl.

94. The composition according to claim 93, wherein the lower alkyl group contains 1-3 carbon atoms.

95. The composition according to claim 93, wherein lower alkyl is methyl.

96. The composition according to claim 93, wherein halogen is fluorine.

97. The composition according to claim 93, wherein $R_{19}$ is hydrogen, trifluoromethyl, difluoromethyl or mono-fluoromethyl or methyl.

98. The composition according to claim 93, wherein $R_{18}$ is hydrogen or fluorine, $R_{16}$ is hydrogen, fluorine or methyl or $R_{16}$ and $R_{18}$ taken together with the carbon to which they are attached form an epoxide ring and $R_{17}$ is hydrogen or methyl.

* * * * *

UNITED STATES PATENT AND TRADEMARK OFFICE
CERTIFICATE OF CORRECTION

PATENT NO. : 5,175,154

DATED : December 29, 1992

INVENTOR(S) : Arthur Schwartz

It is certified that error appears in the above-identified patent and that said Letters Patent is hereby corrected as shown below:

Column 1, lines 34-35: "dehydroepiandorsterone" should read --dehydroepiandrosterone--

Column 12, line 34: "phosphorohloroidite" should read --phosphorochloridite--

Column 12, line 36: "reached" should read --reacted--

Column 36, line 62: "sodium sodium" should read --sodium, sodium--

Column 41, line 19: after "18" insert --[for preparation, see Herzog, et al., JACS $\underline{82}$, 748 (1964)]--

Column 45, line 47: after "following" insert --are prepared--

Column 60, line 2, Claim 46: after "has" insert --the formula:--

UNITED STATES PATENT AND TRADEMARK OFFICE
CERTIFICATE OF CORRECTION

PATENT NO. : 5,175,154
DATED : December 29, 1992
INVENTOR(S) : Arthur Schwartz

It is certified that error appears in the above-identified patent and that said Letters Patent is hereby corrected as shown below:

Column 63, line 10, Claim 66:

"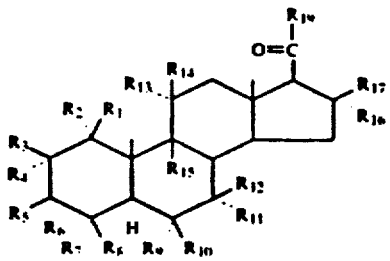"    should read as:

-- 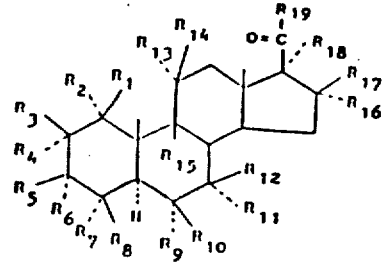 --

Column 64, lines 39-40: "in which the compound has the" should read --which has the--

Signed and Sealed this

Twenty-fifth Day of January, 1994

*Attest:*

BRUCE LEHMAN

*Attesting Officer*   Commissioner of Patents and Trademarks